US012059557B2

(12) United States Patent
Boonzaier et al.

(10) Patent No.: US 12,059,557 B2
(45) Date of Patent: Aug. 13, 2024

(54) MEDICATION DELIVERY DEVICE WITH SENSING SYSTEM

(71) Applicant: Eli Lilly and Company, Indianapolis, IN (US)

(72) Inventors: James Angus Boonzaier, Cambridge (GB); Clark Berg Foster, Mission Viejo, CA (US); Kimberly Ann Ringenberger, Zionsville, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 1325 days.

(21) Appl. No.: 16/462,394

(22) PCT Filed: Dec. 8, 2017

(86) PCT No.: PCT/US2017/065251
§ 371 (c)(1),
(2) Date: May 20, 2019

(87) PCT Pub. No.: WO2018/111709
PCT Pub. Date: Jun. 21, 2018

(65) Prior Publication Data
US 2019/0314581 A1 Oct. 17, 2019

Related U.S. Application Data

(60) Provisional application No. 62/434,684, filed on Dec. 15, 2016.

(51) Int. Cl.
*A61M 5/315* (2006.01)
*A61M 5/24* (2006.01)
*A61M 5/31* (2006.01)

(52) U.S. Cl.
CPC ...... *A61M 5/31568* (2013.01); *A61M 5/2422* (2013.01); *A61M 5/31525* (2013.01);
(Continued)

(58) Field of Classification Search
CPC ............ A61M 5/31568; A61M 5/2422; A61M 5/31525; A61M 5/31528; A61M 5/31546;
(Continued)

(56) References Cited

U.S. PATENT DOCUMENTS 685,091 A 10/1901 Becton
1,625,035 A 4/1927 Lilly
(Continued)

FOREIGN PATENT DOCUMENTS

EP 0338806 10/1989
EP 0498737 8/1992
(Continued)

OTHER PUBLICATIONS

Office action dated Jun. 15, 2020 issued from the Japan Patent Office pertaining to patent application No. 2019-530068.
(Continued)

*Primary Examiner* — Lauren P Farrar
(74) *Attorney, Agent, or Firm* — Arthur C. H. Shum

(57) ABSTRACT

A medication delivery device is equipped with a sensing system to determine the amount of a dose set and/or delivered by operation of the device. Such amount is determined based on the sensing of relative rotational and/or axial movements during dose setting or delivery between members of the medication delivery device, where the sensed movements are correlated as applicable to the amount of the dose set. The device includes one or more wiper assemblies coupled to one or more rotatable device members. Sensing bands are coupled to another device member, and arranged in contacting relationship with wipers. During relative rotation and/or axial movement between the device members,
(Continued)

each sensing band is operable to generate an output associated with the relative angular and/or linear position of the wiper along an operational angular length of the sensing bands indicative of relative rotational positions of the device members.

20 Claims, 15 Drawing Sheets

(52) U.S. Cl.
CPC .... *A61M 5/31528* (2013.01); *A61M 5/31546* (2013.01); *A61M 2005/3125* (2013.01); *A61M 2005/3126* (2013.01); *A61M 5/31551* (2013.01); *A61M 2205/3317* (2013.01); *A61M 2205/3561* (2013.01); *A61M 2205/3569* (2013.01)

(58) Field of Classification Search
CPC ...... A61M 5/31551; A61M 2005/3125; A61M 205/3126; A61M 2205/3317; A61M 2205/3561; A61M 2205/3569
See application file for complete search history.

(56) References Cited

U.S. PATENT DOCUMENTS

| | | |
|---|---|---|
| 2,853,586 A | 9/1958 | Vercesi |
| 3,399,368 A | 8/1968 | Elliott et al. |
| 3,723,061 A | 3/1973 | Stahl |
| 4,315,252 A | 2/1982 | Tagami |
| 4,486,891 A | 12/1984 | Kimoto et al. |
| 4,529,401 A | 7/1985 | Leslie et al. |
| 4,552,055 A | 11/1985 | Foxwell |
| 4,592,745 A | 6/1986 | Rex et al. |
| 4,865,591 A | 9/1989 | Sams |
| 4,883,472 A | 11/1989 | Michel |
| 4,931,041 A | 6/1990 | Faeser |
| 5,279,586 A | 1/1994 | Balkwill |
| 5,418,362 A | 5/1995 | Lusby et al. |
| 5,509,905 A | 4/1996 | Michel |
| 5,536,249 A | 7/1996 | Castellano et al. |
| 5,569,212 A | 10/1996 | Brown |
| 5,582,598 A | 12/1996 | Chanoch |
| 5,593,390 A | 1/1997 | Castellano et al. |
| 5,626,566 A | 5/1997 | Petersen et al. |
| 5,628,309 A | 5/1997 | Brown |
| 5,674,204 A | 10/1997 | Chanoch |
| 5,688,251 A | 11/1997 | Chanoch |
| 5,691,646 A | 11/1997 | Sasaki |
| 5,704,922 A * | 1/1998 | Brown .............. A61M 5/31525 604/207 |
| 5,728,074 A | 3/1998 | Castellano et al. |
| 5,743,889 A | 4/1998 | Sams |
| 5,820,602 A | 10/1998 | Kovelman et al. |
| 5,827,232 A | 10/1998 | Chanoch et al. |
| 5,920,198 A | 7/1999 | Suzuki et al. |
| 5,921,966 A | 7/1999 | Bendek et al. |
| 5,925,021 A | 7/1999 | Castellano et al. |
| 5,938,642 A | 8/1999 | Burroughs et al. |
| 5,954,700 A | 9/1999 | Kovelman |
| 5,957,896 A | 9/1999 | Bendek et al. |
| 5,961,496 A | 10/1999 | Nielsen et al. |
| 6,001,089 A | 12/1999 | Burroughs et al. |
| 6,004,297 A | 12/1999 | Steenfeldt-Jensen et al. |
| D425,990 S | 5/2000 | Gravel et al. |
| 6,068,615 A | 5/2000 | Brown et al. |
| 6,080,090 A | 6/2000 | Taylor et al. |
| 6,110,152 A | 8/2000 | Kovelman |
| 6,192,891 B1 | 2/2001 | Gravel et al. |
| 6,221,046 B1 | 4/2001 | Burroughs et al. |
| 6,221,053 B1 | 4/2001 | Walters et al. |
| 6,235,004 B1 | 5/2001 | Steenfeldt-Jensen et al. |
| 6,248,095 B1 | 6/2001 | Giambattista et al. |
| 6,277,099 B1 | 8/2001 | Strowe et al. |
| 6,302,855 B1 | 10/2001 | Lav et al. |
| 6,340,357 B1 | 1/2002 | Poulsen et al. |
| 6,482,185 B1 | 11/2002 | Hartmann |
| 6,540,672 B1 | 4/2003 | Simonsen et al. |
| 6,558,320 B1 | 5/2003 | Causey, III et al. |
| 6,585,698 B1 | 7/2003 | Packman et al. |
| 6,663,602 B2 | 12/2003 | Moller |
| 6,781,522 B2 | 8/2004 | Sleva et al. |
| 6,875,195 B2 | 4/2005 | Choi |
| 7,138,806 B2 | 11/2006 | Gafner et al. |
| 7,195,616 B2 | 3/2007 | Diller et al. |
| 7,704,238 B2 | 4/2010 | Diller et al. |
| 7,992,460 B2 | 8/2011 | Bochen et al. |
| 8,049,519 B2 | 11/2011 | Nielsen et al. |
| 8,197,449 B2 | 6/2012 | Nielsen et al. |
| 8,529,520 B2 | 9/2013 | Daniel |
| 8,556,865 B2 | 10/2013 | Krulevitch et al. |
| 8,672,899 B2 | 3/2014 | Diller et al. |
| 2001/0013774 A1 | 8/2001 | Noltemeyer et al. |
| 2002/0013522 A1 | 1/2002 | Lav et al. |
| 2002/0020654 A1 | 2/2002 | Eilersen |
| 2002/0120235 A1 | 8/2002 | Enggaard |
| 2002/0177923 A1 | 11/2002 | Steffen |
| 2003/0006209 A1 | 1/2003 | Stefen et al. |
| 2005/0182358 A1 | 8/2005 | Veit et al. |
| 2005/0182360 A1 | 8/2005 | Yeandel et al. |
| 2007/0123829 A1 | 5/2007 | Atterbury et al. |
| 2008/0140018 A1 | 6/2008 | Enggaard |
| 2009/0318865 A1 | 12/2009 | Moller et al. |
| 2010/0106098 A1 | 4/2010 | Atterbury et al. |
| 2012/0238960 A1 | 9/2012 | Smith et al. |
| 2013/0072897 A1 | 3/2013 | Day et al. |
| 2013/0310756 A1 | 11/2013 | Whalley et al. |
| 2014/0074041 A1 | 3/2014 | Pedersen et al. |
| 2014/0171879 A1* | 6/2014 | Butler .............. A61M 5/31541 604/218 |
| 2014/0194829 A1 | 7/2014 | Baek et al. |
| 2014/0243750 A1 | 8/2014 | Larsen et al. |
| 2015/0018775 A1 | 1/2015 | Groeschke et al. |
| 2015/0174330 A1 | 6/2015 | Nagel et al. |
| 2015/0320934 A1 | 11/2015 | Draper et al. |
| 2015/0343152 A1 | 12/2015 | Butler et al. |
| 2016/0008552 A1 | 1/2016 | Madsen et al. |
| 2016/0136353 A1 | 5/2016 | Adams |
| 2016/0259913 A1 | 9/2016 | Yu et al. |
| 2016/0287804 A1* | 10/2016 | Madsen .............. G01D 5/1655 |
| 2016/0296702 A1 | 10/2016 | Rasmussen et al. |
| 2016/0378951 A1 | 12/2016 | Gofman et al. |
| 2017/0023204 A1 | 1/2017 | Takeuchi et al. |
| 2017/0128674 A1 | 5/2017 | Butler et al. |
| 2017/0189625 A1 | 7/2017 | Cirillo et al. |
| 2017/0274148 A1 | 9/2017 | Mews et al. |

FOREIGN PATENT DOCUMENTS

| | | |
|---|---|---|
| EP | 0519137 | 12/1992 |
| EP | 0581925 | 2/1994 |
| EP | 0615762 | 9/1994 |
| EP | 0778034 | 6/1997 |
| EP | 0937471 | 8/1999 |
| EP | 0937472 | 8/1999 |
| EP | 1043037 | 10/2000 |
| EP | 1074273 | 2/2001 |
| EP | 1095668 | 5/2001 |
| EP | 1240913 | 9/2002 |
| EP | 2060284 | 5/2009 |
| EP | 2468340 | 6/2012 |
| EP | 2692378 | 2/2014 |
| GB | 2309801 | 9/1997 |
| JP | 2005-508205 | 11/2002 |
| JP | 2008-516709 | 5/2006 |
| JP | 2015-506771 | 8/2013 |
| WO | 9009202 | 8/1990 |
| WO | 9619872 | 6/1996 |
| WO | 0041754 | 7/2000 |
| WO | 0077472 | 12/2000 |
| WO | 0110484 | 2/2001 |
| WO | 0156635 | 8/2001 |

(56) References Cited

FOREIGN PATENT DOCUMENTS

| | | |
|---|---|---|
| WO | 0159570 | 8/2001 |
| WO | 02064196 | 8/2002 |
| WO | 02092153 | 11/2002 |
| WO | 03009461 | 1/2003 |
| WO | 03015838 | 2/2003 |
| WO | 03005891 | 11/2003 |
| WO | 2006045525 | 5/2006 |
| WO | 2011064299 | 6/2011 |
| WO | 2012004298 | 1/2012 |
| WO | 2013010893 | 1/2013 |
| WO | 2013098421 | 7/2013 |
| WO | 2014037331 | 3/2014 |
| WO | 2014128157 | 8/2014 |
| WO | 2015002806 | 1/2015 |
| WO | 2015123688 | 8/2015 |
| WO | 2016180873 | 11/2016 |
| WO | 2017021226 | 2/2017 |
| WO | 2017092960 | 6/2017 |
| WO | 2017165207 | 9/2017 |
| WO | 2018031390 | 2/2018 |
| WO | 2018111708 | 6/2018 |
| WO | 2018111709 | 6/2018 |

OTHER PUBLICATIONS

Eli Lilly and Company, Technical Dossier for the HumaPen® Pen-Injector Family, Aug. 15, 2000, pp. 1 and 10-25 provided.
Soft Pot potentiometers https://media.digikey.com/pdf/Data%20Sheets/Spectra%20Symbol/SP%20Series%20SoftPot.pdf.
Hoffman-Krippner potentiometers http://www.hoffmann-krippner.com/potentiometers-sensofoll.html.
State Electronics potentiometers http://www.potentiometers.com
International Search Report pertaining to International Application No. PCT/US2017/065251; Date of Mailing: Mar. 27, 2018.
Written Opinion of the International Searching Authority pertaining to International Application No. PCT/US2017/065251; Date of Mailing: Mar. 27, 2018.
Datasheet for the FlexiPot Strip Position Sensor, available from Tekscan, Inc.; accessed Jun. 1, 2023 at FLX-Datasheet-FlexiPot-RevD.pdf (tekscan.com).

\* cited by examiner

MEDICATION DELIVERY DEVICE WITH SENSING SYSTEM

BACKGROUND

The present disclosure pertains to medication delivery devices, and, in particular, to a sensing system in a medication delivery device.

A variety of medication delivery devices, including for example pen injectors, infusion pumps and syringes, are commonly used for periodic administration of medications. It is important that the proper amount of medication be supplied at the appropriate times as the health of the patient is at stake. In many instances, failure to accurately deliver the appropriate amount of medication may have serious implications for the patient.

The administration of a proper amount of medication requires that the actual dosing by the medication delivery device be accurate. The term "dosing" as used herein refers to two phases of administering a dose, namely, setting the dose amount and delivering the amount of the set dose.

Medication delivery devices often utilize mechanical systems in which various members rotate or translate relative to one another. In most instances, these relative movements between members are proportional to the dose amount set and/or delivered by operation of the device. Accordingly, the art has endeavored to provide reliable systems that accurately measure the relative movement of members of a medication delivery device in order to assess the dose set and/or delivered.

While useful, prior art sensing systems are not without their shortcomings. For instance, some sensing systems take up more space within a delivery device than is desirable, resulting in a delivery device that is more bulky or inconvenient to use, or in a delivery device that has to sacrifice one or more features to have room in a compact device for the sensing system. Some sensing systems use relatively expensive componentry, or may be overly complicated so as to adversely impact the cost of manufacture or potentially the system reliability.

Thus, it would be desirable to provide a medication delivery device with a sensing system that can overcome one or more of these and other shortcomings of the prior art.

SUMMARY

Examples of a medication delivery device are provided herein. According embodiment of the present disclosure, the device includes a first member and a second member rotatable relative to the first member about an axis of rotation in proportion to at least one of an amount of a dose set and an amount of a dose delivered by operation of the medication delivery device. A wiper assembly is coupled to the first member, having a pair of radially projecting wipers. A first electrically operable sensing band and a second electrically operable sensing band each are coupled to the second member. Each of the sensing bands is arranged radially disposed relative to and in contacting relationship with the wipers. During relative rotation between the first and second members, each of the sensing bands is operable to generate outputs associated with the relative angular position of the wiper along an operational angular length of each of the sensing bands that is indicative of relative rotational positions of the first and second members. A controller is electrically coupled with the sensing band to determine, based on the outputs generated by each of the sensing bands, at least one of the amount of the dose set and the amount of the dose delivered by operation of the medication delivery device. In another embodiment, the device may include additional rotational wiper assemblies and corresponding sensing bands. In another embodiment, the device may include one or more linear wiper assemblies and corresponding linear sensing bands.

BRIEF DESCRIPTION OF THE DRAWINGS

The above-mentioned and other features of this present disclosure, and the manner of attaining them, will become more apparent, and the invention itself will be better understood, by reference to the following description of embodiments of the present disclosure taken in conjunction with the accompanying drawings, wherein.

Figure 1:
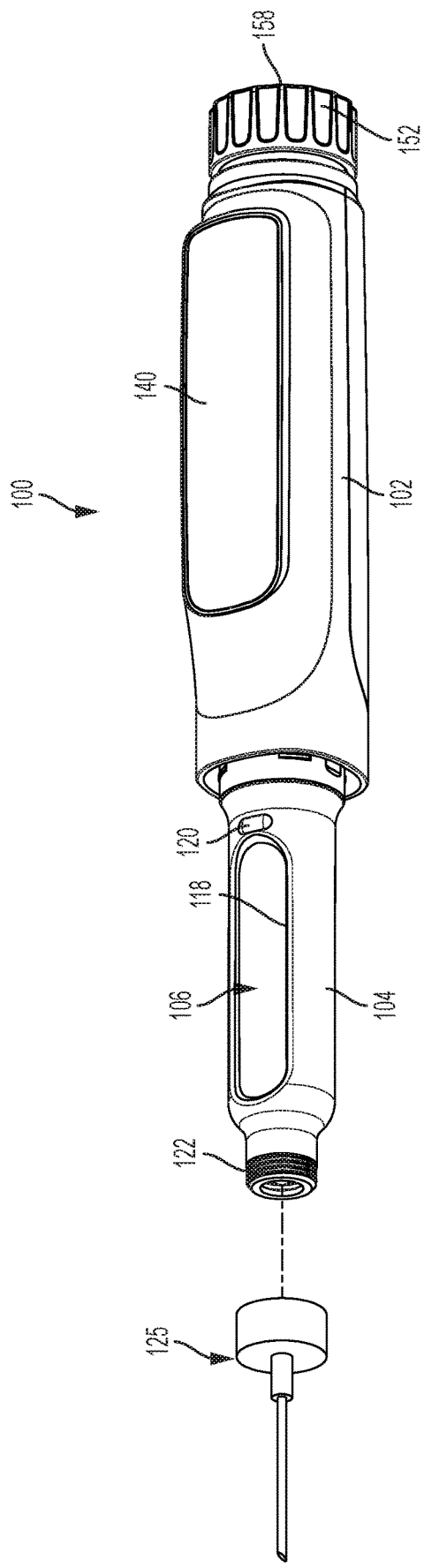
FIG. 1 is a perspective view of an exemplary medication delivery device in the form of an injection pen without a cap and prior to a mounting of a needle assembly.

Corresponding reference characters indicate corresponding parts throughout the several views. Although the drawings represent embodiments of the present disclosure, the drawings are not necessarily to scale, and certain features may be exaggerated or omitted in some of the drawings in order to better illustrate and explain the present disclosure.

DETAILED DESCRIPTION

Figure 2:
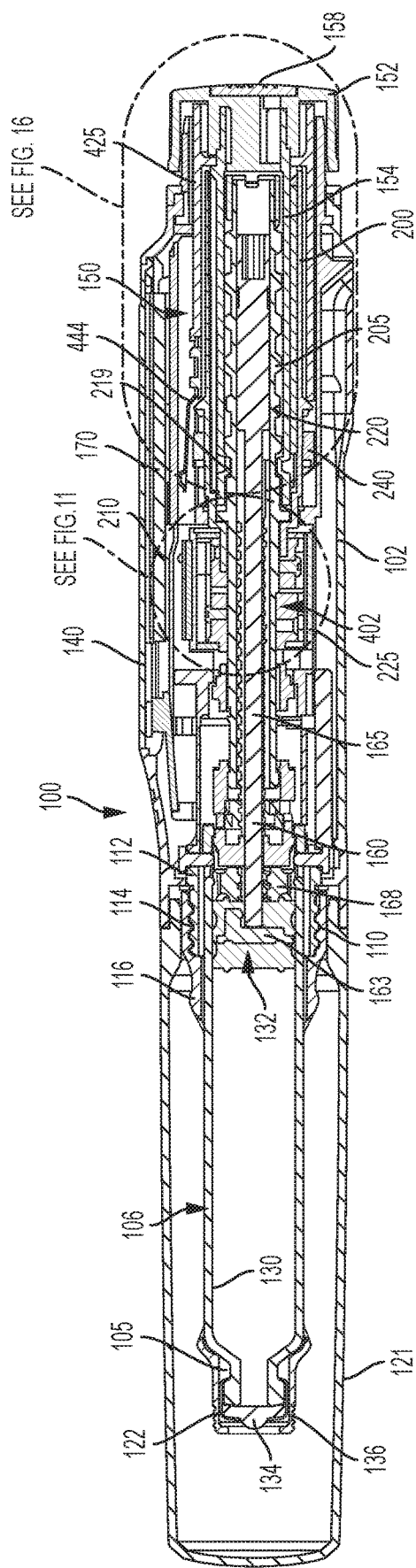
FIG. 2 is a side view in longitudinal cross-section of the injection pen of FIG. 1 with a protective cap.

Referring now to FIGS. 1 and 2, there is shown a medication delivery device 100 equipped with a sensing system that is described further as being used to determine the amount of a dose set by operation of the device. Such amount is determined based on the sensing of relative rotational and/or axial movements during dose setting between members of the medication delivery device, where the sensed movements are correlated as applicable to the amount of the dose set. In different embodiments, the sensing system is configured to determine the amount of at least one of the dose set and the dose delivered by operation of the device, or alternatively, both the amount of the dose set and the amount of the dose delivered by operation of the device. One of the advantages of the disclosed embodiments is that a medication delivery device with sensing system may be provided that can accurately and reliably assess the amount of medication that has been set and/or delivered by that device. Another of the advantages of the disclosed embodiments is that a medication delivery device with sensing system may be provided that requires a limited number of individual parts. Still another of the advantages of the disclosed embodiments is that a medication delivery device with sensing system may be provided which has a compact form factor. Another of the advantages may be the elimination for system calibration and hardware resets.

The shown device is a reusable pen-shaped medication injection device, generally designated 100, which is manually handled by a user to selectively set a dose and then to inject that set dose. The description of device 100 is merely illustrative as the sensing system can be adapted for use in variously configured medication delivery devices, including differently constructed pen-shaped medication injection devices, differently shaped injection devices, and infusion devices. The medication may be any of a type that may be delivered by such a medication delivery device, such as insulin for example. Device 100 is intended to be illustrative and not limiting as the sensing system described further below may be used in other differently configured devices. Device 100 is similar in many respects to a device described in U.S. Pat. No. 7,195,616, which is incorporated herein by reference in its entirety.

As used herein, the term "coupled" encompasses any manner by which a first item is caused to move in unison with or in proportion to a second item as the second item moves. Items are rotationally coupled if they are caused to rotate together. Coupling systems may include, for example, connections provided through splines, gears or frictional engagement between the members, or similar connections provided by other components which indirectly couple the members. Where applicable, an item may be coupled to another item by being directly positioned on, received within, attached to, or integral with the other item, or otherwise secured thereto, directly or indirectly.

The term "fixed" is used to denote that the indicated movement either can or cannot occur. For example, a first member is "rotatably fixed with" or "fixed against rotation relative to" a second member if the first member is not able to rotate relative to the second member.

With reference to FIG. 1, medication injection device 100 includes an outer housing that supports the internal components of the device. The housing is shown as having a rear or main housing 102 and a forward or cartridge housing 104. Main housing 102 is configured to hold a drive assembly of the device, which assembly is a strictly user powered, mechanical assembly as described but may in alternate embodiments be a motorized assembly. Cartridge housing 104, also known as the cartridge retainer, is configured to hold a cartridge 106 filled with medication to be delivered by device operation. With reference to FIG. 2, cartridge retainer 104 is detachably connectable or mountable to main housing 102 via external threading 110 on a protruding collar portion 112 of main housing 102 which mates with internal threading 114 on a ring portion 116 at the proximal end of cartridge retainer 104. Suitable detachable connecting elements other than threadings 110 and 114 are known in the art and naturally may be employed, such as a bayonet fitting, or the use of an additional latching component.

Cartridge retainer 104 includes an internal hollow 105 suited to removably receive cartridge 106, thereby allowing a cartridge to be inserted therein, and then removed therefrom when depleted and replaced with a fresh cartridge of similar design. Openings 118 in cartridge retainer 104 allow visibility of the cartridge contents. A detent feature 120 provided on the exterior of cartridge retainer 104 allows for a protective cap 121 to be detachably mounted over the cartridge retainer 104 when a needle assembly 125 (shown in FIG. 1) is not attached to the cartridge retainer 104, as shown in FIG. 2. Although cartridge retainer 104 is described herein as being a reusable component, the cartridge retainer 104 can be integrated with, and therefore be disposable with, the cartridge 106.

Medication cartridge 106 is of conventional design, including a barrel 130 having an interior reservoir filled with medication which is sealed at one end by a slidable plunger or piston 132 and sealed at the other end by a septum 134 held by a crimp ring 136.

Needle assembly 125 is detachably mountable to an externally threaded distal end 122 of cartridge retainer 104 pierces the septum 134 when so mounted. The pierced septum through which the needle extends serves as an outlet during dispensing for the medication within the reservoir of barrel 130, which medication is delivered through the needle assembly 125 by operation of device. 100. The cartridge 106 can hold multiple doses of medication, or even a single dose, depending on the purpose of device 100.

Medication injection device 100 is shown in FIGS. 1-2 in its "zero position" at which the device has not been set for delivery of any dose. This zero position setting may be indicated by the number "0" or zero somewhere on the device, such as, for example, visible on an electronic dose display 140 shown in FIG. 1. Device 100 is arranged after being manipulated to set a dose, such as, for example, thirty units for delivery, and the number "30" or thirty would be visible somewhere on the device such as, for example, on the display 140.

Medication injection device 100 is typical of many such reusable devices including a manually-powered dose delivery mechanism, generally designated 150, that controls forward or distal advancement of a drive member, generally designated 160. Drive member 160 advances within the cartridge barrel 130 to directly engage and advance plunger 132. As shown in FIG. 2, dose delivery mechanism 150 includes a dose knob 152 connected via a drive sleeve or tube 154 to a mechanical drive assembly, indicated generally at 156, that is housed within main housing 102. When knob 152 is turned by a user to set a dose for injection, dose knob 152 and tube 154 screw out proximally together from main housing 102. When a user applies a plunging distal force on the proximal end 158 of dose knob 152, the resulting purely translational axial motion of dose knob 152 and tube 154 distally forward into main housing 102 is converted by drive assembly 156 into a smaller motion of drive member 160 forward from main housing 102 into the interior of cartridge barrel 130.

In one example, drive member 160 is formed in two pieces including a forward end 163 that directly engages the cartridge plunger 132, and a shaft 165 that axially extends rearward from forward end 163 into main housing 102. The shaft 165 is threaded and is engaged with drive assembly 156 to be screwed out from main housing 102 and thereby driven forward. Shaft 165 is shown threadedly engaged with a housing bulkhead 168. Housing bulkhead 168 is shown integral with main housing 102 but, in another example, may be separately formed and fixedly attached thereto. Forward end 163 is provided in the form of an enlarged foot that is mounted on shaft 165 to allow relative rotation, allowing foot 163 to engage plunger 132 without relative rotation therebetween as shaft 165 screws out. The foot 163 and shaft 165 may be a two-piece construction of drive member 160, when shaft 165 screws out from the housing during advancement. In another example, the foot and shaft of the drive member may be a single piece drive member for simply translation as it is forced forward from the housing.

Device 100 may use an electronic dose display 140, as shown, rather than a helically marked dial display as used in many other reusable injection devices. Display 140 is circuited to and controlled by an electronic controller or computing assembly 170 mounted within main housing 102. Controller 170 can include conventional components such as, for example, a processor, power supply, memory, etc. Controller 170 is programmed to achieve the electronic features of device 100, including causing the display of set doses. The set dose displayed in display 140 is determined by the interaction of dose delivery mechanism 150 with a sensing system, generally shown at 402, which is electrically circuited with controller 170. The controller includes control logic operative to perform the operations described herein, including detecting a dose delivered by medication delivery device based on a detected rotation of the dose setting member relative to the actuator. The controller is operable to determine the dose setting by determining the dose setting member position, such as the dose dial, based on rotational and/or linear position of respective components, which is determined by associating the electrical characteristic (such as voltage or resistance) from the respective sensor bands and the number of rotations to an exact and/or absolute position from a database, look up table, or other data stored in memory. The controller is operable to determine the dose delivery by determine the dose setting member position, such as the dose dial, based on rotational and/or linear position of respective components, which is determined by associating the electrical characteristic (such as voltage or resistance) from the respective sensor bands and the number of rotations to an exact and/or absolute position from a database, look up table, or other data stored in memory. The controller is operative to store the detected dose in local memory (e.g., internal flash memory or on-board EEPROM). The controller is further operative to wirelessly transmit a signal representative, of the detected dose to a paired remote electronic device, such as a user's smartphone, over a Bluetooth low energy (BLE) or other suitable short or long-range wireless communication protocol. Illustratively, the BLE control logic and controller are integrated on a same circuit.

With additional reference to FIGS. 3-7, in another example of a sensing system 175 for use in device 100 and for coupling to one or more rotatable members (two members shown) of device 100 which, when a dose is set by a user screwing dose knob 152 out from housing 102, are relatively rotatable in proportion to the amount of such set dose. Depending on the configuration of device 100 and in particular the drive assembly 156, the rotatable members of device 100 to which sensing system 175 is coupled also can be rotatable relative to each in proportion to the amount of a dose delivered by plunging operation of dose knob 152, and in which case sensing system 175 can additionally be used in determining the delivered dose. Alternatively, in another embodiment where dose delivered instead of dose set is sensed, sensing system 175 is positioned for sensing dose delivered by being coupled to one or more rotatable members (two members shown) of device 100 which, during dose delivery, are relatively rotatable in proportion to the amount of dose delivered, but which two member's do not relatively rotate during dose setting.

Figure 3:
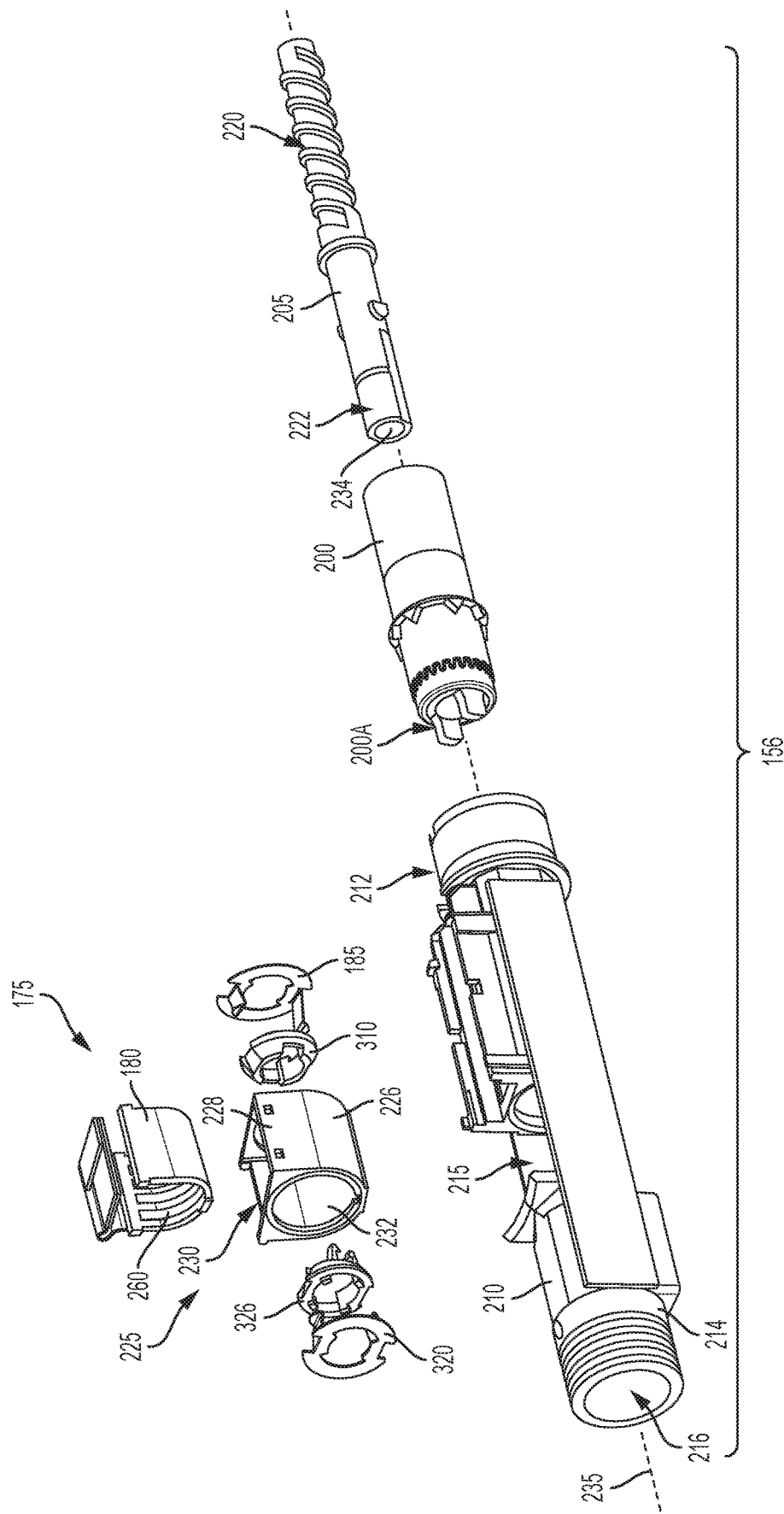
FIG. 3 is a perspective view, in partially exploded form, of portions of an exemplary medication delivery device with an example of a sensing system.
Figure 4:
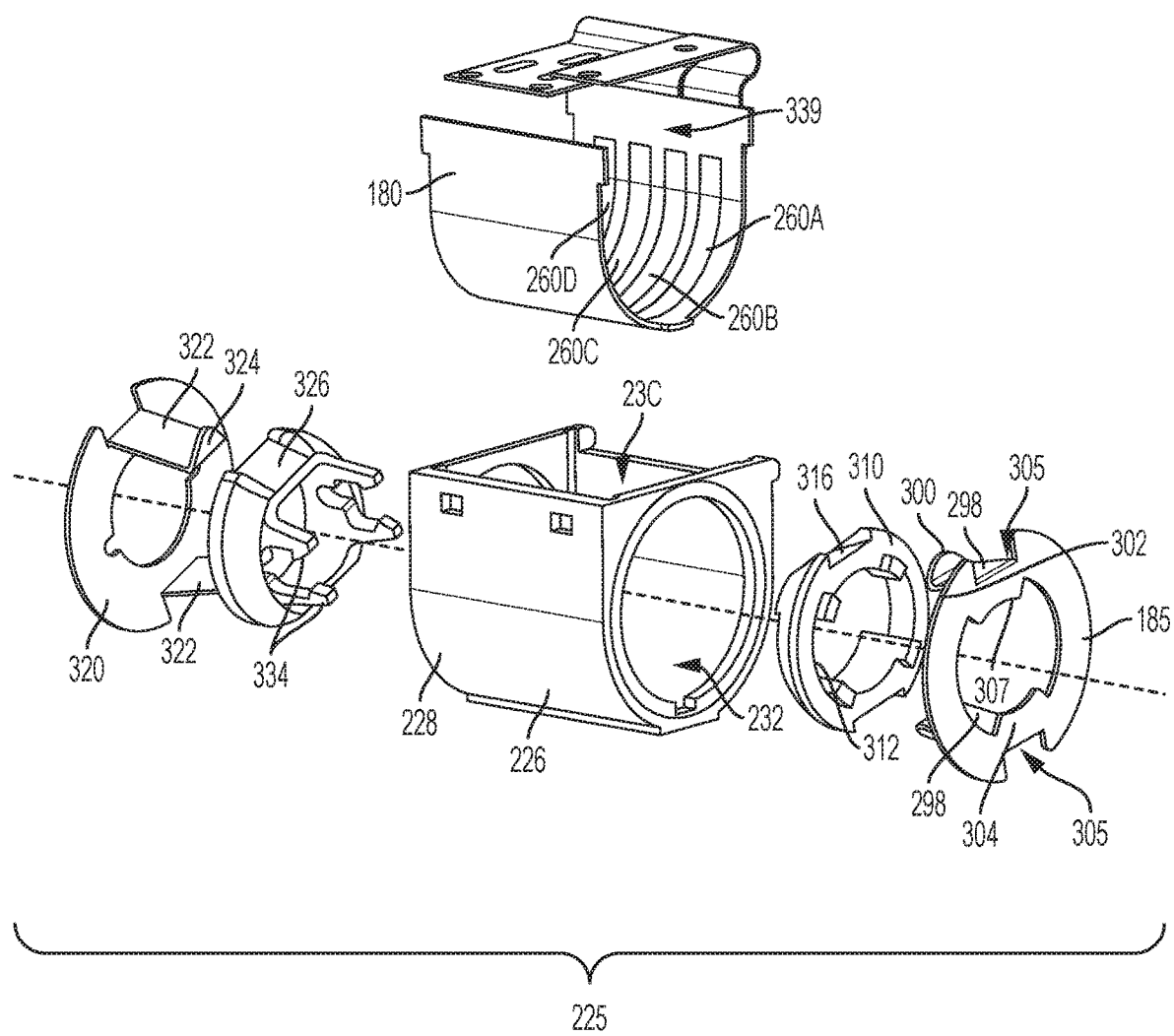
FIG. 4 is an exploded perspective view of components of a sensor mount assembly for the sensing system in FIG. 3.

Sensing system 175 operates to detect relative rotational positions of the one or more rotational members (first and second device members such as a barrel 200 and a drive sleeve 205 shown in FIG. 2) to which it is coupled and generates outputs correlated to such relative rotational positions. In FIG. 3, sensing system 175 includes a sensor 180 (shown including one or more sensing bands 260) and one or more wipers (shown as wiper 185). Various embodiments of wiper and sensor combinations are described herein. It is noted that the number of wiper and sensor combinations may vary due to the drive mechanism of the device and/or the kind of information from the drive, mechanism needed to determine dose setting and/or dose delivery. In one example, where only one of dose setting or dose delivery, the device 100 may include a single wiper, that is, any one of the wipers disclosed herein, coupled to a diver mechanism component, that is, any of the ones disclosed herein, and a sensor suitably placed for sensing wiper position. For example, in device 100, sensor 180 is coupled to the housing or housing component, and wiper 185 is coupled to a part of drive assembly 156 that at select times of device use rotates within the housing interior. Sensor 180 alternatively can be coupled to housing via one or more intermediate components, and further alternatively can be coupled to housing 102, either directly or indirectly, to not rotate relative to the housing but be free to move axially. The wiper 185 may be configured to move axially, along with the barrel, during device use, and sensor 180 may be attached directly to a component that is rotatably fixedly, and axially movably, mounted to the housing 102 such that the wipers and sensing bands are in alignment for sensing.

In one example, sensing system 175 is coupled to select members of device 100 which are relatively rotatable in proportion to the amount of the set dose, and which are relatively rotatable in proportion to the amount of the injected or delivered dose. In one example, the rotational members include the tubular barrel 200 and the drive sleeve 205 being coaxially positionable within a chassis housing 210 having a tubular configuration. The chassis housing 210 includes a barrel proximal portion 212 axially separated from a drive sleeve distal portion 24 by a sidewall aperture 215 sized to receive a portion of the sensing system. The chassis housing 210 includes a longitudinal bore 216 sized to receive the barrel 200 that is coaxially positioned over and slidably engaged to the tube 154 that is threadably engaged with the drive sleeve 205. In one example, a proximal interior surface of the barrel 200 fits over the tube 154 having an internal threading 219 engageable with an external threading proximal portion 220 of the drive sleeve 205. The non-external threaded distal portion 222 of the drive sleeve 205 extends along a distal interior surface of the barrel 200 and distally beyond the barrel 200 axially through the sidewall aperture 215 into the drive sleeve distal portion 210.

A sensor mount assembly 225 is sized to fit within the sidewall aperture 215 and axially adjacent relative to the barrel portion 212 and the drive sleeve portion 214 of the chassis housing 210. The sensor mount assembly 225 includes the sensor 180 and a sensor mount 226 including a sidewall 228 defined into a tubular configuration. A portion of the sidewall 228 is omitted to define a receiving opening 230 sized to receive the sensor 180, as well as the lid to fit over the omitted portion. The extended distal 222 portion of the drive sleeve 205 extending beyond the proximal end of the barrel 200 fits through the lumen 232 of the sensor mount 226 and the sensor. The sensor mount assembly 225 can include wiper and/or bearing components as described below.

Barrel 200 is a sleeve that is keyed to rotate with, but be axially movable relative to, tube 154. The drive sleeve 205 includes external threading 220 that is engaged by internal threading 219 of tube 154. An internal axial hollow 234 of drive sleeve 205 threadably receives threaded shaft 165 therein. A not shown keying between drive sleeve 205 and threaded shaft 165 means that a rotation of drive sleeve 205 within chassis housing 210 causes a corresponding rotation of shaft 165 which advances that shaft axially to eject medication from the device 100.

During dose setting, as knob 152 and tube 154 are turned to screw out proximally axially together from the device housing, barrel 200 rotates within the housing about longitudinal axis 235 of rotation while drive sleeve 205 does not rotate about axis 235 of rotation due to a not shown spline connection between the device housing 102 and drive sleeve 205.

When dose knob 152 is plunged by a user to deliver a dose, that plunging initially produces a transitioning translational movement of drive sleeve 205, due to an axial force transmitted by tube 154 at the external threading 222, which due to an axial force transmitted by a sleeve flange to a barrel shoulder causes a transitioning translational movement of barrel 200. This transitioning movement does not cause tube 154 and barrel 200 to rotate because a torque required to overcome a spring-biased, housing-engaging dose clicker (not shown) splined to barrel 200 is greater than the torque generated at the threading 222. This translational movement, occurring against a resistive axial force provided by the not shown clicker spring, moves splines 240 of barrel 200 axially into engagement with not shown complementary housing splines while releasing the not shown spline connection between the device housing and drive sleeve 205. Further user plunging of dose knob 152 causes drive sleeve 205 and thereby shaft 165 to rotate about axis 235 of rotation, causing medicament to be ejected, while barrel 200 does not rotate about axis of rotation due to its splined connection with the housing.

Sensor 180 may be directly attached, such as with an adhesive, to the interior circumferential and radially inwardly facing surface 250 of sensor mount 226, or alternatively along the housing 102 or housing component, such as a chassis housing 210. Sensor 180 is configured to generate an electrical output based on where along its angularly extending operational length it is directly contacted by wiper 185. Sensor 180 is arranged within the sensor mount 226 in a curved shape around axis 235 of rotation, and the sensor 180 is disposed radially outward of wiper 185. Sensor 180 may be annular in shape to extend the full 360 degrees of the housing internal circumference and completely ring the axis of rotation.

Sensor 180 can include a membrane potentiometer manufactured in the curved shape to facilitate assembly within device 100 to remove residual stresses. One suitable sensing band is available from Tekscan Incorporated. In one example, the sensor 180 includes first and second substrates or backing strips and first and second electrical strips and that sandwich a spacer element. Substrates and spacer may be made of a pliable plastic that is electrically non-conductive such as PET (polyethylene terephthalate) or a polymide film such as Kapton. Alternatively, the spacer can be a printed material deposited directly onto either substrate by means such as screen printing. The spacer may serve to keep the electrical strips apart absent a sufficient force applied by the wiper, which may also have an adhesive property to connect the substrates together. The substrates and the outer edges of the spacer can form the exterior of the sensor 180, and, when sealed together along their peripheral regions, protectively encase strips. Strips may be secured to the substrates and/or the spacer, or can be otherwise formed such as screen printed, for example, directly to the substrates.

Electrical strips when in a neutral state are held within sensor 180 in spaced relationship due to the interposition of the spacer. When sensor 180 is in its curved configuration within device 100, the strip is disposed radially inward of the other strip, and absent an external force the strips are radially spaced resulting in no electrical connection therebetween. In this radially spaced relationship, strips are directly facing each other through the central slot-shaped opening within the spacer. Not shown dielectric projections also can be provided on one of the electrical strips within the opening to ensure the strips remain so radially spaced absent a wiper induced movement. Such projections can be provided, such as by screen or jet printing, in any suitable pattern that maintains the strip radial spacing, such as discrete bumps arranged in a polka dot pattern, parallel ribs oriented axially that span the strip width and which are spaced from each other along the length of the strip, parallel ribs oriented at an angle relative to the strip width which span that strip width and which are spaced from each other along the length of the strip, or parallel ribs oriented circumferentially that span the strip length and which are spaced from each other along the width of the strip.

The first electrical strip is operable as an electrical resistor element that has an electrical resistance that varies linearly along its strip length that extends between a first angular end and a second angular end. A first electrical lead is circuited with and extends from end of the first strip, and a second electrical lead is circuited with and extends from end of the first strip. The second lead is routed near the electrical strip side to the lead end parallel to the second lead which facilitates the electrical connection of the sensor 180 with the device circuitry. The other electrical strip is operable as an electrical conductor element with very low electrical resistance, such as made of silver, copper or gold, having a length that extends between a first angular end and a second angular end. A first electrical lead of the second strip is circuited with and extends from end of the second strip. While the leads are positioned in an extension of the substrates that extends in the angular direction along the lengths of such substrates, in an alternate embodiment such leads can be routed to an alternate substrate portion that alternatively or additionally extends laterally, or in the axial direction, from the substrates to facilitate an electrical connection.

The second strip is sufficiently flexible along its length to allow its deflection in the outward radial direction, at the point where it is acted upon, through the substrate by wiper 185, to be in direct physical and electrical contact with the first electrical strip. This wiper causes a compression that deflects the second strip radially outward thereat to result in wiper 185 operationally engaging the sensor 180 by causing an electrical contact between the first and second electrical strips thereat, but with the strips otherwise remaining radially spaced. The resistance between electrical lead of the second strip and the lead of the first strip while the wiper is in contact (sensor produces no value when no contact) varies linearly with the distance between the angular end and the point of contact between first and second strips. The resistance between electrical lead of the second strip and the other lead of the first strip varies linearly with the distance between the second angular end and the point of contact between strips. The resistance between the electrical leads of the first strip is equal to the sum of the electrical resistance between lead of the second strip and the first lead of the first strip and the resistance between lead of the second strip and the second lead of the first strip. In an alternate embodiment, and provided resistor element first strip may have flexibility properties similar to that of conductor element second strip to allow a deflection by wiper engagement, sensor 180 can be configured to have resistor element second strip be radially inward of conductor element first strip.

The linear alignment of the first and second strips of the sensor 180 defines an effective operational sensing band 260 of the sensor 180. Sensing hand 260 is exactly circumferentially wrapped around the axis 235 of rotation so as to minimize the use of axial space within device 100 devoted to sensing system 175. Band 260 can alternatively have its ends axially offset so that band 260 is arranged as a helix. Sensing band 260 is operational to sense wiper 185 at any point along its angular operational length of sensing band 260 at which electrical strips are present and capable of being brought into electrical contact by a radial deflection caused by wiper 185. Sensing band 260 has an electrical characteristic correlated with where along its angular operational length it is operationally engaged due to the physical contact with wiper 185. The angular operational length of sensing band 260 for which sensing is effective is less than 360 degrees around the axis 235 of rotation for the wrapping of the band 260. As a result, the operational angular length extends less than 360 degrees around the housing inner circumference, and in particular 360 degrees minus the portion of the inner circumference spanned by a spacer end region. One suitable operational length can be in the range of 180 to 200 degrees, and in other examples, a length of 185 degrees to 190 degrees in operational angular length may be used. As shown, the sensor 180 may include a plurality of sensing bands (sensing bands 260A-D) disposed axially spaced from one another along the axis 235.

Wiper 185 may be directly attached, such as with an adhesive, mechanically coupled, or by being integrally formed therewith, to an outer radial surface, of a part of the drive assembly 156. In another example, wiper 185 may be a component coupled with a part of the drive assembly 156. Drive assembly 156 can take various forms, but typically involves multiple interacting parts, and wiper 185 is shown positioned on a rotatable part of this assembly so as to have direct contacting access to the sensor 180.

The sensing system may include a barrel wiper and a barrel sensor forming a first subassembly sized to couple to the end of the barrel as shown and a drive sleeve wiper and a drive sleep bearing forming a second subassembly sized to fit around the extended portion of the drive sleeve. In one example, wiper 185 includes a support body 296 and an arm 298 that projects longitudinally along the axis 235 of rotation from support body 296. A portion of the arm 298, such as, for example, an end or tip of the arm 298 may contact the sensing band 260 of sensor 180. In one example, a tab 300 may be coupled to the free end 302 of the arm 298 to form a contacting tip. Tab 300 may project radially outward from the arm 298 for contacting the sensing band 260 which is disposed radially outside relative to the arm and tab. Tab 300 is shown along the free end 302 may have a rounded apex or outwardly facing, convex surfaces that provides a precise point of contact for sliding engagement with sensing band 260 along the circumferential extent of the band. Wiper arm 298 may have an axially extending length parallel to the axis 235, about which rotates the part of the drive assembly 156 from which the wiper projects. As no electrical current is routed through it, wiper 185 can be formed entirely of an electrically non-conductive material such as a thermoplastic elastomer such as silicone. The term "wiper" used herein may refer to any part of the wiper, such as, for example, the arm and/or tab or any portion of the wiper body. To this end, the support wiper body 296 may include first and second wipers, which refers to the two radially projecting portions (shown in the figures as the arm/tab configuration).

The wiper support body 296 may include a disk body including an outer radial surface and an inner radial surface. A coupled end 304 of the arm 298 may be coupled to the body 296 such as extending from its inner radial surface as shown. In one example, the wiper is formed as an integral component including the wiper support body 296 and a pair of arms 298 extending longitudinally from the inner radial surface of the body. The arms 298 may be disposed at opposite sides of the body 296. Radial notches 305 may be located along the wiper support body 296 at locations corresponding to the location of the arms. The radial notches 305 can be formed from the outer radial surface radially into an intermediate section of the body 296. The radial notches 305 may have variety of shapes and sizes, such as, for example, a square notch as shown. In some examples, a radial extension 307 may be defined along the inner radial surface corresponding to the location of the notches 305. Such radial extensions 307 may be sized and shaped for coupling with the drive assembly component. The wiper 185 alternatively can be a single point contact, without the arm 298 as shown. The wiper need not extend the width, as extending in the axial direction, of the resistor strip within sensing band 260. Providing wiper 185 with an axial length can account for both tolerances within the design of the device as well as axial motion within the device of the wiper 185 relative to the sensor 180 and housing 102.

The radial extension of the arm(s) 298 and/or the tab 300 is sized and shaped to span the annular space or gap within the housing interior between sensor 180 and drive assembly 156. The tab 300 of wiper 185 projects sufficiently radially outward to provide at least a minimum application force and thereby operationally engage sensing band 260 as described further below. Such force can be controlled by the manufacturer through the material selection and processing, such as tempering, as well as the geometry of the wiper and wiper arm and/or tab and its residual compression within. To better ensure a proper engagement with sensor 180 at all operational angular positions of the drive assembly 156, and thereby wiper 185, relative to housing 102, wiper 185 can be biased radially outward from drive assembly 156. Such a biasing force can be provided by a material resiliency resulting from forming wiper 185, arm and/or tab out of a durable but elastic material such as a thermoplastic elastomer or butyl rubber with a suitable durometer. The biasing force can also or alternatively be provided by the shape of the arm and/or tab (such as a leaf spring configuration) or an additional spring element acting in a radial direction between wiper 185 and drive assembly 156. Still further, a biasing of the sensing bands 260 radially inwardly, such as by placing spring elements to act radially between the outer radial periphery of the sensing bands and the housing radial interior surface, can be done alternatively or additionally.

Wiper 185 and sensor 180 are in radial alignment when active to sense relative rotational positions. In device embodiments where for example the drive assembly 156 moves axially from one state, where the sensing system 175 is not used, to a second state, at which the sensing system 175 is used, the wiper 185 and sensor 180 can be axially spaced when not being used.

Figure 6:
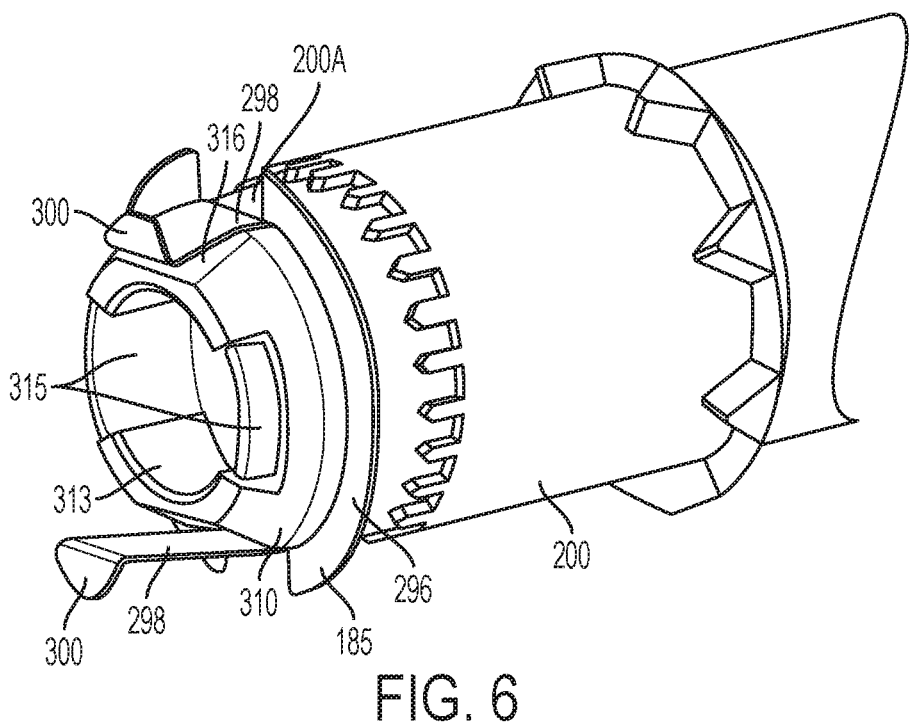
FIG. 6 is a partial perspective view of assembled device portions from FIG. 3, including a barrel, a barrel wiper and a barrel bearing.

The wiper 185 may include a bearing 310 to form a subassembly. The bearing 310 is configured to rigidly connect, both rotationally and axially, to the corresponding drive assembly component, such as with a combination of rotary keys and axial clips or other suitable system. Bearing 310 includes an annular shaped body having an axial bore to receive the corresponding drive assembly component. With reference to FIG. 6, the bearing 310 includes axial notches 312 formed along an inner radial surface 313 of the bearing 310 that are sized and shaped to receive axially extending radial tabs 315 extending from the distal end 200A of the barrel 200 for secure attachment. The wiper 185 is securely coupled to the bearing 310 by a combination of rotational key features and/or axially by adhesive bonding. In one example, the bearing 310 may include planar notched surfaces 316 formed along the outer radial surface of the bearing to rotationally lock and securely fix the wiper to the bearing. The wiper arms 298 are configured to project axially beyond the proximal end of the bearing such that the arms are disposed along the planar surfaces 316. Other wiper shapes than the one shown in FIG. 3 can be used to activate sensor 180. Such additional wiper shapes include round protrusions, or journaled disks or cylinders that result in rolling contact with sensor 180.

Figure 7:
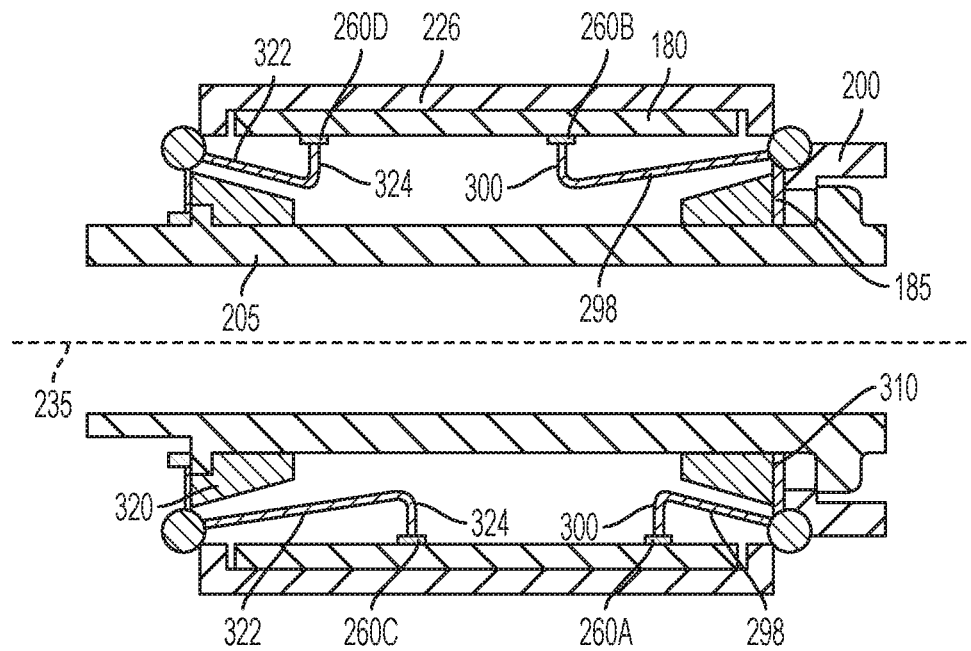
FIG. 7 is an abstract, longitudinal cross-sectional view of a portion of the medication delivery device with sensing system of FIG. 3 when assembled, illustrating the wipers and sensor bands engagement.

In one example, the wiper 185 and the bearing 310 are associated with the barrel 200 to define a barrel wiper and barrel wiper bearing subassembly, such as shown in FIG. 6. The barrel wiper bearing 310 is rigidly connected, both rotationally and axially to the barrel 200, such as with a combination of rotary keys and axial clips or other suitable system. The barrel wiper 185 is shown including two arms 298 and/or tabs 300 and thus serves as a single component one wiper element 298 for one sensing band 260A of a set and another separate wiper 298 for a second sensing band 260B of the set that senses the rotational position of the barrel 200. The pair of arms 298 may be disposed on opposite sides of the wiper, such as substantially 180 degrees (that is, in a range of 180 degrees plus/minus 10 degrees). In one example, the barrel wiper body 296 has a disc shaped body with two leaf spring extension arms, 180° opposed, with sensor contact tabs 300 directed radially outward. The first tab 300 of the first arm 298 may be axially offset from the second tab 300 of the second arm 298 of the pair of arms. In one example, each of arms 298 may extend longitudinally to different lengths. In one example, the arms 298 extend axially to different lengths such that tabs 300 are axially offset (such as shown in FIG. 7) so that each one corresponds separately with a single sensing band of a sensing band set 260A, 260B. The barrel wiper tabs 300 apply a force radially outwards on the corresponding sensing band, thereby activating the sensing band 260A, 260B at a distance along its length that correlates with an angular rotational position of the barrel 200.

For devices with a second wiper element, a second wiper 320 may be included. The second wiper 320 may be directly attached, such as with an adhesive, mechanically coupled, or by being integrally formed therewith, to an outer radial surface of a part of the drive assembly 156. In another example, wiper 320 may be a component coupled with a part of the drive assembly 156. Drive assembly 156 can take various forms, but typically involves multiple interacting parts, and wiper 320 is shown positioned on a rotatable part of this assembly so as to have direct contacting access to the sensor 180. The second wiper 320 may include, features of the wiper 180, such as the arms 322 and tabs 300, the description of the features for wiper 180 is adopted for the second wiper 320. However, it is noted that the arm(s) 322 of the second wiper 320 are extending in the proximal direction and the arms 298 of the wiper 185 extend in the opposite direction, the distal direction, to point toward one another. The arms 298, 322 of each wiper are shown along the same axial circumferential region of the device; however, the arms may be circumferentially offset from one another. Also, when the tabs 300, 324 are axially offset, it is noted that the longer of the arms are circumferentially offset, that is, the longer arm 322 is at the top as shown and the longer arm 298 is at the bottom as shown.

Figure 5:
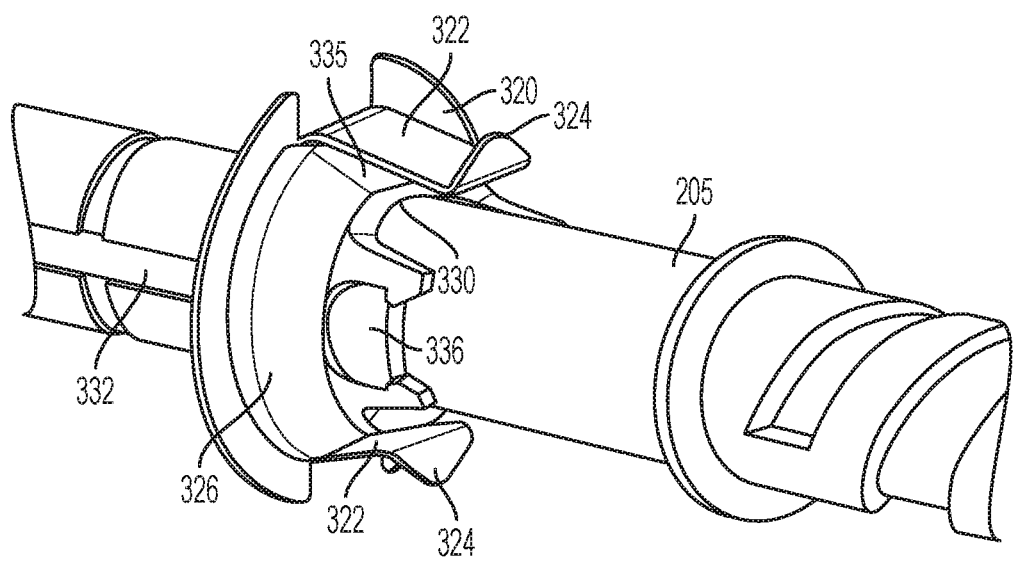
FIG. 5 is a partial perspective view of assembled device portions from FIG. 3, including a drive sleeve, a drive sleeve wiper and a drive sleeve bearing.

The second wiper 320 may include a second bearing 326 to form a subassembly. In one example, the wiper 320 and the bearing 326 are associated with the drive sleeve 205 to define a drive sleeve wiper and drive sleeve, wiper bearing subassembly, such as shown in FIG. 5. The bearing 326 is configured to rigidly connect, both rotationally and axially, to the corresponding drive assembly component, such as with a combination of rotary keys and axial clips or other suitable system. Bearing 326 includes an annular shaped body having an axial bore to receive the corresponding drive assembly component. With reference to FIG. 5, the bearing 326 may include, axial notches (not shown) formed along an inner radial surface 330 of the bearing 326 that are sized and shaped to receive radial key 332 extending along the outer surface of the drive sleeve 205 for secure attachment. Alternatively, or in addition to, the bearing 326 may include flexible finger latches 334 extending from the proximal end 326A of the bearing to cooperatively engage a radial protrusion 336 extend from the outer surface of the drive sleeve 205. The finger latches 334 are operable to inhibit relative rotational and axial movement between the wiper/bearing and the drive sleeve. The wiper 320 is securely coupled to the bearing 326 by a combination of rotational key features and/or axially by adhesive bonding. In one example, the bearing 326 may include planar notched surfaces 335 formed along the outer radial surface of the bearing 326 to rotationally lock and securely fix the wiper to the bearing. The wiper arms 322 are configured to project axially beyond the distal end of the bearing 326 such that the arms are disposed along the planar surfaces 335.

Figure 8:
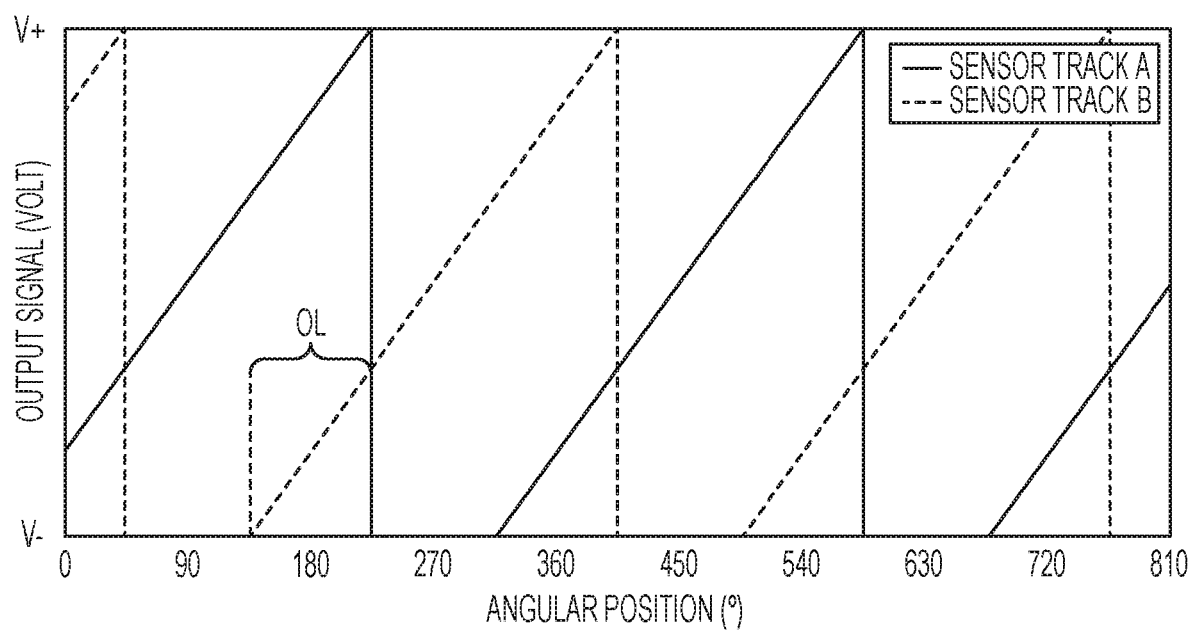
FIG. 8 is a chart illustrating the electrical signals received by the controller which are output from a set of sensor bands and wipers for one of the sensed rotating parts, either the barrel or the drive sleeve of the medication delivery device with sensing system of FIG. 3, during the rotational operation of that sensed rotating part.

FIG. 7 depicts illustratively a cross-sectional view of the first and second wipers 185, 320, the first and second wiper bearings 310, 326, and sensor 180 assembled together according to an exemplary embodiment. The first wiper 185 has two contact tabs 300 and thus serves as a single wiper element with a first tab 300 for one sensing band 260A and with a second tab 300 for another sensing band 260B of that set. The second wiper 320 has two radially outward contact tips 324 and thus serves as a single wiper element with a first tip 324 for one sensing band 260O and with a second tip 324 for another sensing band 260D of that set. The 180° offset tips are axially offset within the device so that each one corresponds with a single sensing band of a sensing band set. Wiper tips apply a force radially outwards on the corresponding sensing band, thereby activating the sensing band at a distance along its length that correlates with an angular position of the drive sleeve. In the illustrative embodiment, for a given wiper-sensing band combination or set, the interaction between the wipers and sensing bands takes place over slightly more than 180° (due to the bands or sensor arc being greater than 180° and the wiper spring preload maintaining contact for a small portion beyond the curved section), therefore, there is a handover period during which both wipers are in contact, therefore the signal is 'always-on'. Each sensing band of the set produces an independent output to the controller, thus there is adequate data for the controller software to deal with the handover period. FIG. 8 illustrates the expected output signal for upper angular position of a wiper set (for example, axially offset tabs 324) and a corresponding set of sensing bands (260C—"Sensor Track A; 260D "Sensor Track B"). FIG. 8 exaggerates for purposes of illustration the overlap or handover period (labelled OL), and is shown as being 90 degrees of overlap which is 45 degrees on either side of the normal handover position (typically 180 degrees apart). The signals are shown for 810 degrees of rotation of the sensed element, such as the barrel or drive sleeve, relative to the housing during device operation. In one example, the wiper assembly having a pair of radially projecting wipers in contact with corresponding pair of sensing bands permits the detection of the complete rotation (360 degrees) of the relavent device component for accommodating the overlap or handover period by having at least one of the wipers in contact with the corresponding sensing band.

In one example, the first and second bearings 310, 326 include external cylindrical bearing surfaces that mate with corresponding cylindrical bearing surfaces on the sensor mount 226. The sensor mount 226 may be supported by the drive sleeve 205 and barrel 200 via the corresponding bearing components. This promotes true running of the wipers relative to the sensor mount and the sensors in turn. The first wiper 185 and the second wiper 320 may incorporate an outer flange formed by the disk wiper body, which acts as a thrust bearing against the sensor mount 226. To this end, the sensor mount 226 is 'trapped', or axially constrained, between the two wipers 185, 320, such that the sensor mount 226 tracks the axial motion of the drive sleeve 205 and barrel 200 when moving axially together within the chassis housing 210 or housing in the device transition between dial dose setting and injection drug delivery modes. As the sensor mount 226 so moves axially with the drive sleeve 205 and barrel 200, the sensing bands 260A-D of sensor 180 on the sensor 180 are constrained to move axially with the drive sleeve 205 and barrel 200 to maintain alignment of the wipers with their respective sensing bands. The controller 170 (FIG. 2) is configured to receive first, second, third and fourth electrical signal outputs from the sensing bands 260A-D, respectively. The device controller is able to determine where along the angular length of the sensing band the wiper element of the first and second wipers operatively contacts, allowing a position of the barrel 200 and/or drive sleeve 205 relative to the sensor mount to be sensed to allow a dose set or dose delivery for the device to be identified by the controller.

The device controller 170 recognizes barrel and/or drive sleeve rotational position from the corresponding electrical signals received from the respective sensing bands 260A-D. During the majority of barrel and/or drive sleeve rotation, the magnitude of the electrical signal to the device controller reflects where the tips of the wipers engage the sensing band of sensor 180. For example, when one of the tabs 300 of the wiper arms 298 of the wiper enter a rotary gap of the sensor 180 (shown in FIG. 4), coming off the sensing band, for example, band 260A, the other tab 300 of the other wiper arm 298 simultaneously engages the other sensing band 260B. This changed signal value, as well as the value of that signal as it further changes as the wiper moves along the angularly length of sensing band 260B, allows the controller 170 to recognize barrel and/or drive sleeve rotational position until the wiper again engages the sensing band 260A while the wiper moves off the sensing band 260B. In such a design, while there would always be at least one wiper arm of a wiper in contact with a sensing band for all possible rotational or angular positions of the relevant sensed member, there also will be certain rotational positions of the sensed member for which wiper engages. At such certain rotational positions, it is appreciated that the signal that one of the sensing bands 260A-D sends to the device controller, depending on the electrical configuration of the sensor, can introduce uncertainty for the controller, such as the output signal being generated by the sensing band being an averaging of the signals otherwise sent by wipers contacting their respective paths. This uncertainty can be resolved in the device by an initialization action involving active rotation of the wiper over a sufficiently large angular distance as to provide the controller with a continuous characteristic signal from the sensing bands to enable the controller to resolve a known reference position.

Controller 170 includes a microprocessor electrically circuited with sensing bands 260A-D of the sensor 180. The electrical signal outputs from the sensing band(s) reach microprocessor and are processed by the microprocessor to identify the amount of the dose set by operation of the device 100, specifically based on the microprocessor determining relevant movement of the drive assembly 156 relative, to the main housing 102 during dose setting. An electrical power source, such as a 1.8 volt source, that is housed within device 100 to provide power to the controller 170. Input leads are connected between the microprocessor and sensing band(s) and may include resistor elements and/or signal processor elements such as filter and amplifiers. Output leads may be connected between the microprocessors and an indicator and/or display system. Due to the voltage signal received by microprocessor being dependent on where along the angular length of resistor element of the wiper has caused resistor element to be contacted by the deflection of conductor element of sensing bands 260A-D, controller 170 can determine the relative positions of the members sensed by sensing system 175, namely the drive assembly 156 and the housing 102. The circuitry results in a differential voltage signal being provided at different input leads to the microprocessor that can be used to compensate for any variations in the output of sensing bands of sensor 180 that can occur over time or due to environmental conditions.

The operational angular length of sensing bands 260A-D being less than three hundred sixty degrees results in a sensing gap around the housing inner circumference. In this embodiment, unless the wiper has an angular length larger than the sensing gap, there is time during the circumferential travel of the wiper that the presence of wiper 185 cannot be actually sensed by the sensing system 175. The controller 170 can be programmed to understand that sensing system 175 not outputting a wiper engagement corresponds to wiper 185, 322 being aligned with the sensing gap. If such a programming is not desired, or if the sensing gap is larger than the angular resolution needed for a particular application, an alternate sensing system can be employed.

In a still further alternate embodiment which is not shown, the sensing circumferential gaps of the two, or even more, sensing bands can be axially aligned. However, the wiper element would have portions on different axial segments of the drive assembly 156, which wiper portions would be appropriately angularly spaced around the drive assembly 156 so as to not all simultaneously engage the sensing gaps of the multiple sensing bands.

Other delivery devices may be equivalent to a Humalog® KwikPen® from Eli Lilly and Company, which is disclosed in U.S. Pat. No. 7,291,132, the entire contents of which are incorporated herein by reference. Further details of dose delivery detection module will be appreciated from U.S. Provisional Patent Application No. 62/362,808 filed Jul. 15, 2016, entitled DOSE DETECTION MODULE FOR A MEDICATION DELIVERY DEVICE, now PCT application No. PCT/US17/41,081, filed Jul. 7, 2017, the entire contents of both which are incorporated herein by reference. Another example of the delivery device is an auto-injector device that may be found in U.S. Pat. No. 8,734,394, entitled "Automatic Injection Device With Delay Mechanism Including Dual Functioning Biasing Member," which is hereby incorporated by reference. In its entirety, where such device being modified with one or more various sensor systems described herein to determine an amount of medication dose set and delivered from the medication delivery device based on the sensing of relative rotation and/or linear displacement within the medication delivery device.

In one illustrated example, the device may include a pair or set of sensing bands 260A-D with a pair of wipers 185, 320. The sensing system 175 of the device includes sensor 180 that uses pairs or sets of sensing bands 260A-D in the form of membrane potentiometers, which sensing bands interact with pairs of wipers also shown in the device. Each wiper 185, 320 may contact only one of the sensing band 260A-D during its use. These potentiometers may have the fundamental construction and behavior as described above with respect to the other embodiments. (The sensing bands may include separate layers, printed with resistive ink, activated by a mechanical wiper, producing a voltage proportional to the distance along the band at which the wiper makes contact.)

The curved portion of the sensing bands 260A-D covers at least 180°, such as 180° as shown. The curved portion, which forms the base of a U-shape arrangement of the sensor, has ends that extend in a straight configuration, or as flanges, which flanges form the legs of the U-shape.

In one example, the sensor 180 incorporates four parallel sensing bands 260A-D or tracks that serve as two pairs of bands in order to sense rotational position of two elements. Each pair of bands corresponds with a rotationally sensed component, i.e. barrel 200 or drive sleeve 205. Each sensing band 260 extends the full angular length of the curved portion and is visible in the figures on the radial interior of the curved portion. The sensing bands 260A-D also continue up along the flanges, which may serve as transition regions for engagement by the wipers 185, 310 and which increase the effective band length. The bands in a given pair of bands (band pairs 260A-B or band pairs 260C-D) have a length the sum total of which spans 360 degrees, plus normally a handover or safety margin. Band pairs with each band being from 185 degrees to 190 degrees in operational angular length may be used, with each band of the pair spanning the same angular distance around the same, or non-angularly staggered, circumferential portion of a different axial segment of a rotating member, or rotationally sensed component. A band need not extend 180 degrees if the effective length of the other band in the pair is sufficiently long. Bands of the same length achieve a desirable symmetry of design. For the curved sensor portion of 180 degrees, each of the transition regions may extend so as to effectively allow wiper engagement of the sensing bands for up to an additional 20 degrees of wiper rotation at each end of the curved sensor portion (or up to 200 degrees).

In one example, the sensor 180 incorporates two continuations, or tails, which provide electrical termination points for the sensor electrical inputs (2× voltage supply) and outputs (4× signal). The tails are on and extend from separate layers of the sensor assembly to avoid the need to bridge between layers. Termination may be pads designed to correspond with pads on a Printed Circuit Board (PCB) of the controller and electrically connected using ACF (anisotropic conductive film) or other non-soldered means. Soldering is generally not desirable due to the presence of plastic substrates. Alternatively, termination may be pads designed for insertion into a standard ZIF (zero force) type connector conventionally used with flexible PCBs.

In one example, the sensor mount 230 of the device includes a single rigid shaped sensor-mounting component, or the 'U-mount'. The sensor mount 230 having the U-mount configuration supports the sensor in its shape. The U-configured sensor mount 230 incorporates mechanical locating features that correspond with locating features on the sensor 180 to position the sensor relatively during assembly. The sensor may be additionally secured to the U-configured sensor mount by adhesive. The sensor mount 230 may incorporate a longitudinal key used to constrain the sensor mount rotationally with respect to the chassis housing 210, or device housing. Apart from the key, the sensor mount 230 is in clearance with the chassis housing 210 at all times. The sensor mount 230 is axially movable within the device relative to the chassis housing 230.

Referring now to FIGS. 9-13, there is shown pertinent parts for medication delivery device 100 with sensing system, generally designated 402, and shown implemented within the device 100 in FIG. 2. The sensing system 402 of device is configured to determine the amount of the dose set and/or the amount of the dose delivered by operation of the device.

Figure 9:
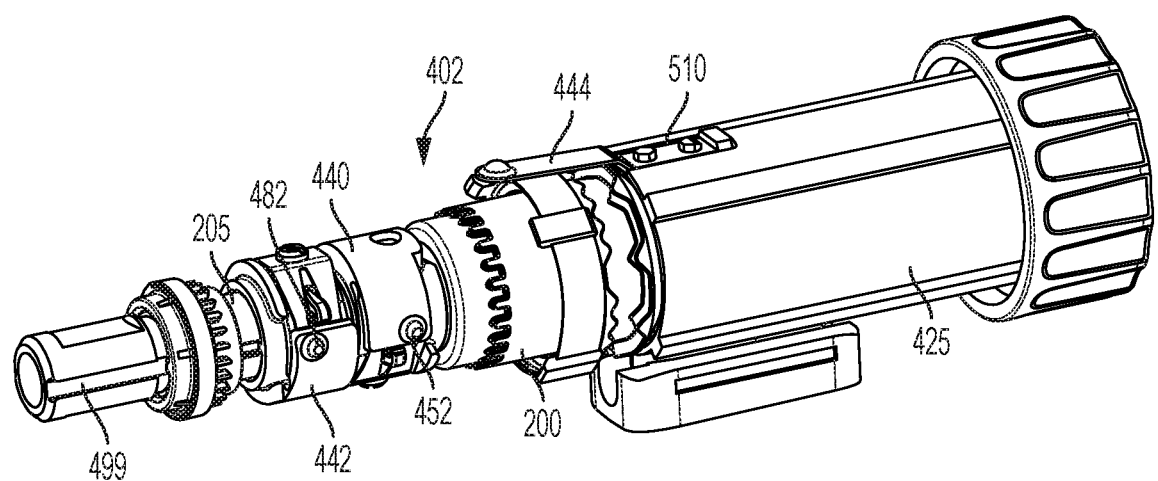
FIG. 9 is a partial perspective view of select portions of the device of FIG. 1 with the sensing system.
Figure 10:
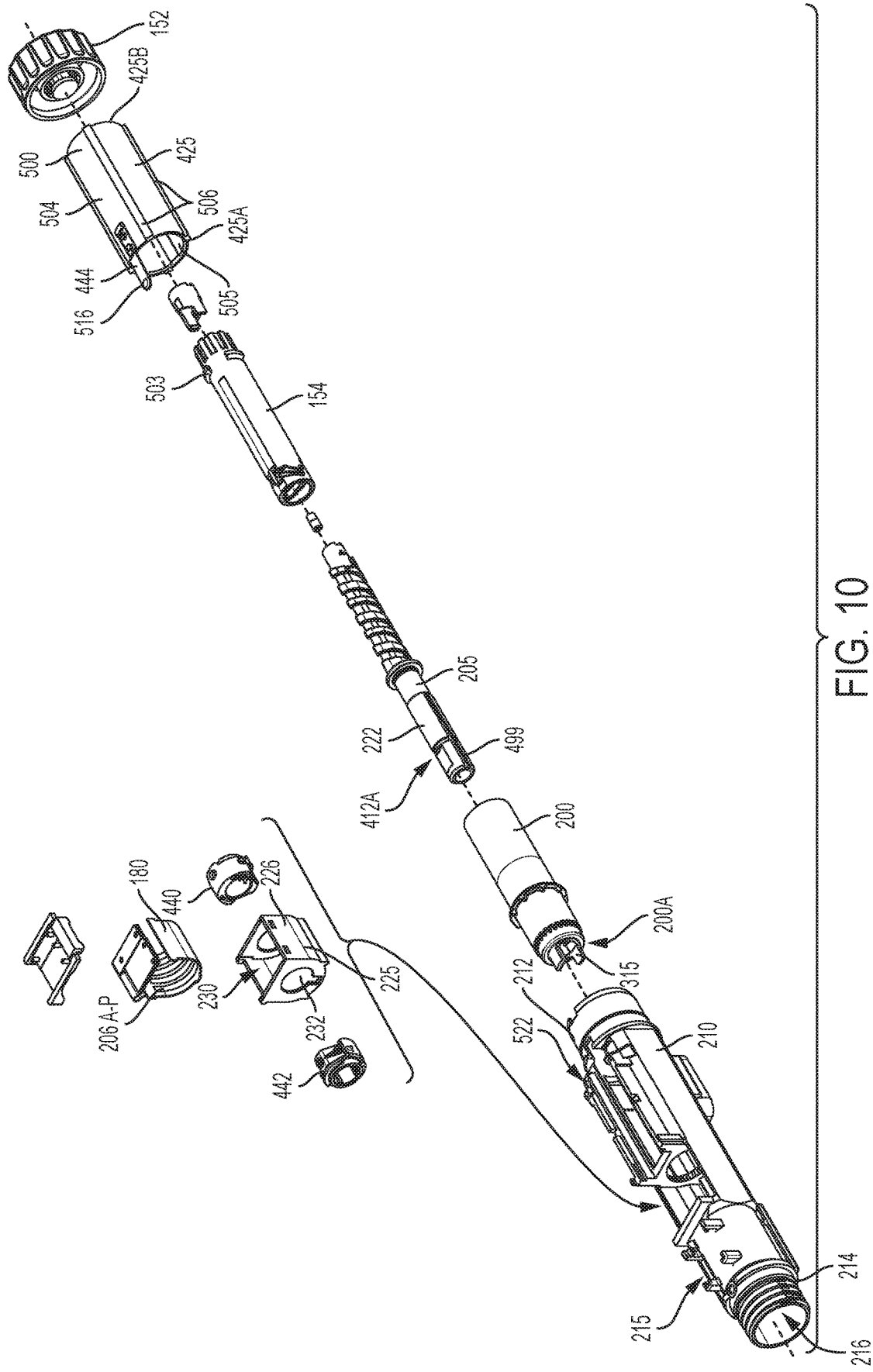
FIG. 10 is a perspective view, in partially exploded form, of portions of the medication delivery device of FIG. 1 with the sensing system of FIG. 9.
Figure 11:
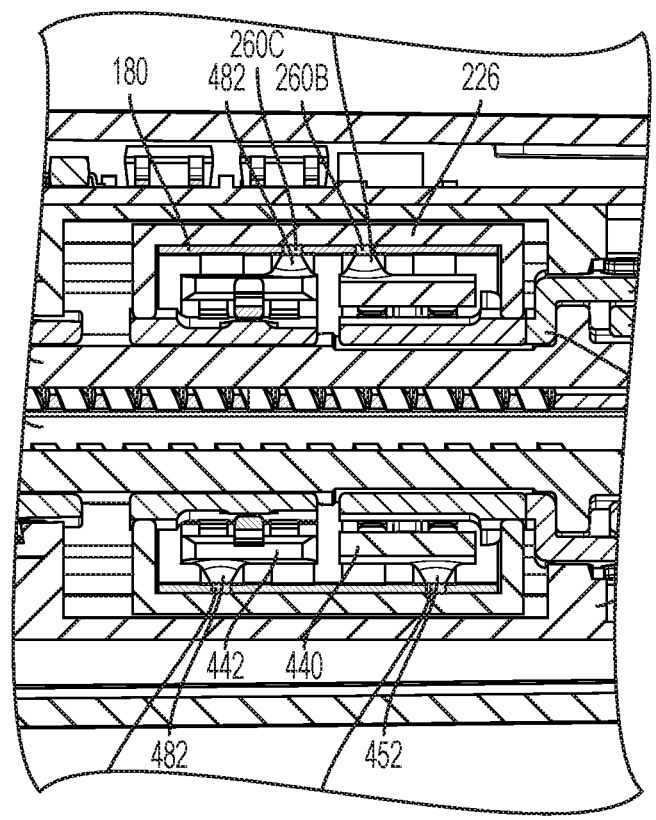
FIG. 11 is a longitudinal cross-sectional view taken from a callout in FIG. 2.
Figure 12A:
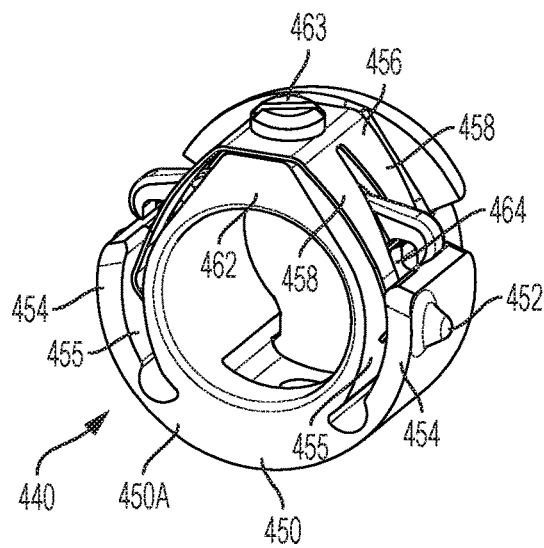
FIGS. 12A-12E are various views of a rotational wiper assembly of the sensing system of FIG. 9.
Figure 12B:
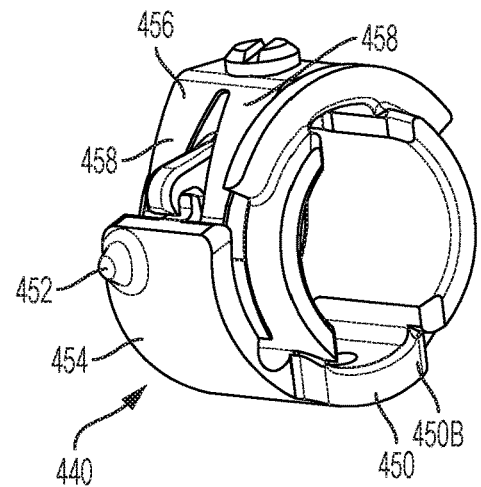
Figure 12C:
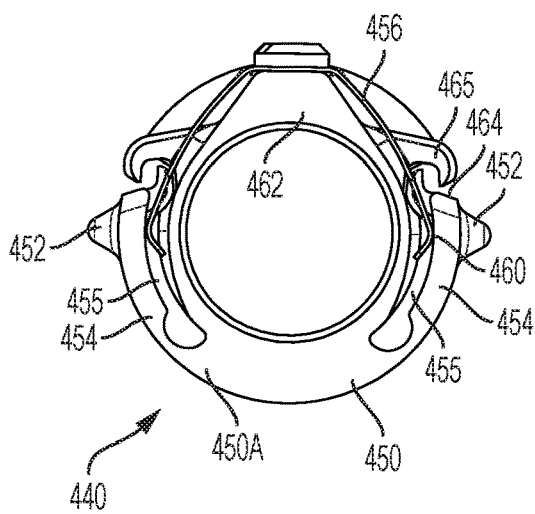
Figure 12D:
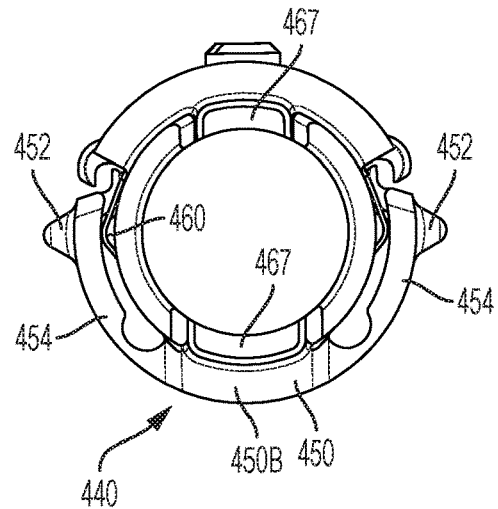
Figure 12E:
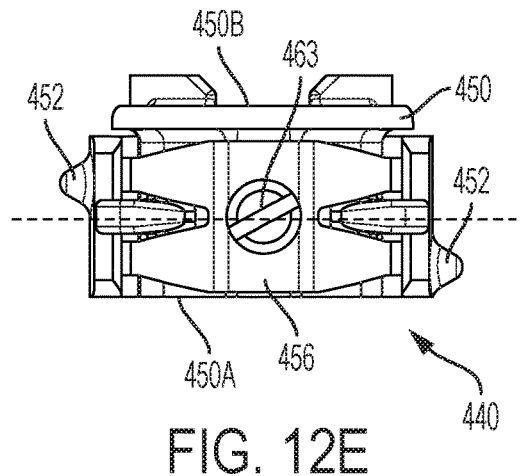
Figure 13A:
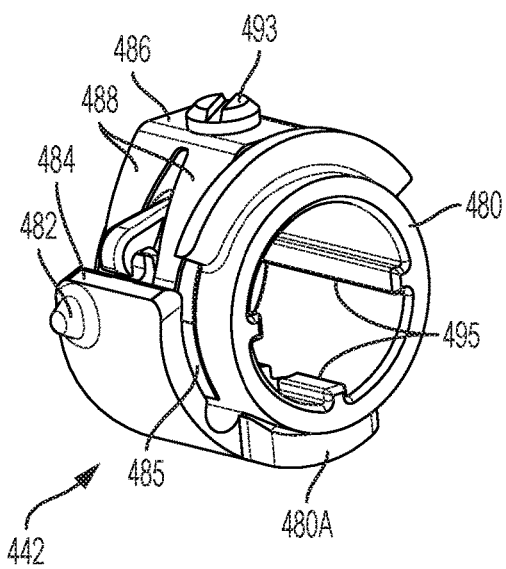
FIGS. 13A-13D are various views of another example of a rotational wiper assembly of the sensing system of FIG. 9.
Figure 13B:
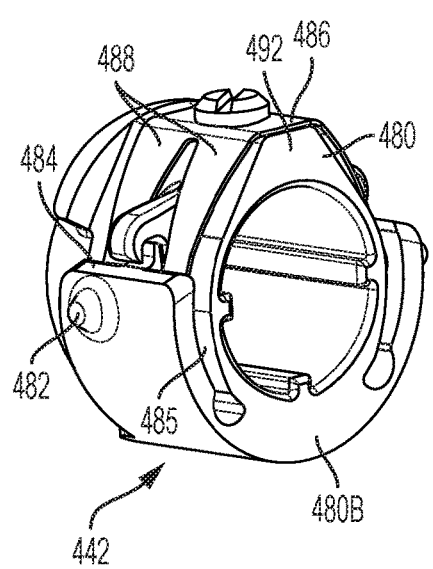
Figure 13C:
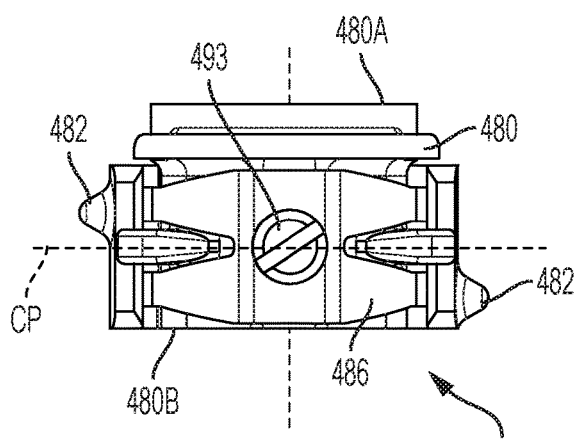
Figure 13D:
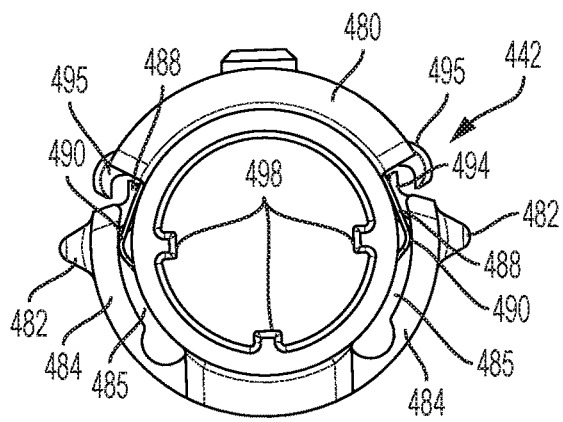

FIG. 9 illustrates yet another example of a sensing system 402 for the device, (with portions omitted for clarity) that incorporates one or more of the features of the sensing system 175. FIG. 10 depicts the device 100 including the barrel 200, the drive sleeve 205 that transmits its rotation, via the mechanical drive train, to the threaded shaft 165 (FIG. 11) used to eject medication, and the chassis housing 210. Also shown is the dial sleeve or tube 154, a linear wiper sleeve 425 (if the linear wiper assembly 444 is provided), and a dose knob 152. The sensing system 402 is shown assembled with the barrel 200 and the drive sleeve 205.

The sensing system 402 includes one or more rotational wiper assemblies, such as, for example, a first rotational wiper assembly 440 (shown securely coupled to the barrel 200) and a second rotational wiper assembly 442 (show securely coupled with the drive sleeve 205). The sensing system 402 may further include linear wiper assembly 444 coupled to the linear wiper sleeve 425 (shown also in FIG. 2) configured to move axially only (allowing for rotation within small tolerances, for example, less than one degree). The linear wiper sleeve 425 is configured to track the axial movement of the dial tube 154. The linear wiper sleeve 425 may be coupled with the dial tube 154 via a thrust bearing interface 445, shown in FIG. 16. The dial tube 154 is configured for rotation during rotation of the dose knob 430 during dose setting, and configured for axial distal translation during linear activation of the dose knob 430 during dose delivery. The linear wiper sleeve 425 proximally translates with the dose knob 430 as the dose knob 430 extends axially farther from the general end of the device 100 during dose setting. The linear wiper sleeve 425 distally translates with the dose knob 430 as the dose knob 430 is pressed into the general device housing during dose delivery. The receiving opening 230 is sized to receive the sensor 180, and is enclosed by a mount lid 441 that fits over the opening 230 and attaches to the sidewall. The extended distal 222 portion of the drive sleeve 205 and the distal end of the barrel 200 fits longitudinally within at least a portion of the lumen 232 of the sensor mount 226 and the sensor 180. The sensor mount assembly 225 is sized to accommodate the first and second rotational wiper assemblies 440, 442 which are coupled to the respective drive sleeve and the barrel.

In FIGS. 12A-12E, the first rotational wiper assembly 440 is shown with a wiper body 450 having a tab 452 at an end of a wiper arm 454. The wiper body 450 is shown including a pair of wiper arms 454 and pair of tabs 452 disposed along opposite sides of the wiper body 450. In one example, the tabs 452 are located along opposite sides of a central plane CP that is orthogonal to the axis. The tab 452 is a protruding body, such as, for example, the conical configuration, extending radially from the arm. The wiper body 450 may include a cylindrical body disposed about the axis between distal and proximal ends (450A, 450B), defining a throughbore sized to permit the drive sleeve to be extended through. The wiper arms 454 may have a semi arcuate configuration. In one example, each of the wiper arms 454 includes a base, opposite the tab end, coupled to a circumferential surface of the wiper body 450 and spaced along the exterior circumferential surface of the wiper body by corresponding gaps 455. In some examples, the wiper arms 454 are integrally formed with the wiper body 450. The wiper arm 454 may be spring biased on its own. In the example shown, the assembly 440 includes a biasing element 456 configured to bias the wiper arm 454 and tab 452 radially outward. The biasing element 456 in one example includes a leaf spring configuration. In another example, the biasing element 456 is shown having a U-shape with a base and legs extending out from opposite sides of the base. The legs may have a split to define a pair of legs 458 on each side of the base. The leg ends 460 of the legs 458 may be disposed between the inside of the wiper arm 454 and the exterior surface of the wiper body 450, pushing radially outward the wiper arms 454. The leg ends 460 may be curved inward.

The wiper body 450 may include a tapered end 462 sized and shaped to receive the biasing element 456 having the U-shaped configuration. The biasing element 456 may be attached to the tapered end 462 by an attachment element 463, such as a fastener. The wiper body 450 may include physical limit elements for each of the wiper arms 454. For example, the wiper arm 454 may include a limit element 464, for example, having a hook configuration, extending from the end of the arm 454. The limit element 464 is configured to engage a body limit element 465 extending from the wiper body in between the splitted legs 458 to limit the radial distance or radial outer extent of the wiper arm can move outward to protect the sensing element. The proximal end 450B of the wiper body 450 may include locking features for engagement with the barrel 200. For example, the wiper body 450 may include one or more axial channels 467 for receiving key or tab structures shown as 315 in FIG. 10) extending from the barrel. The barrel may be coupled with the wiper body of the first rotational wiper assembly by other mechanisms, such as, adhesives, fasteners, or bonding. The distal end 200A of the barrel 200 may include key structures 315 forming a reduced neck portion for insertion into the throughbore defined by the wiper body 450, where the key structures 315 are finally disposed within the axial channels 467.

In FIGS. 13A-D, the second rotational wiper assembly 442 is shown with a wiper body 480 having a tab 482 at an end of a wiper arm 484. The tab may be disposed along any portion of each of the wiper arms 454, 484. The wiper body 480 is shown including a pair of wiper arms 484 and pair of tabs 482 disposed along opposite sides of the wiper body 450. In one example, the tabs 482 are located along opposite sides of a central plane CP that is orthogonal to the axis. The tab 482 is a protruding body, such as, for example, the conical configuration, extending radially from the arm. The wiper body 480 may include a cylindrical body disposed about the axis between distal and proximal ends (480A, 480B), defining a throughbore sized to permit the drive sleeve to be extended through. The wiper arms 484 may have a semi arcuate configuration. In one example, the wiper arms 484 have a base, opposite the tab end, coupled to the wiper body 480 and spaced along the exterior surface of the wiper body by corresponding gaps 485. In some examples, the wiper arms 484 are integrally formed with the wiper body 480. The wiper arm 484 may be spring biased on its own. In the example shown, the assembly 442 includes a biasing element 486 configured to bias the wiper arm 484 and tab 482 radially outward. The biasing element 486 in one example includes a leaf spring configuration. In another example, the biasing element 486 is shown having a U-shape with a base and legs extending out from opposite sides of the base. The legs may have a split to define a pair of legs 488 on each side of the base. The leg ends 490 of the legs 488 may be disposed between the inside of the wiper arm 484 and the exterior surface of the wiper body 480, pushing radially outward the wiper arms 484. The leg ends 490 may be curved inward.

The wiper body 480 may include a tapered end 492 sized and shaped to receive the biasing element 486 having the U-shaped configuration. The biasing element 486 may be attached to the tapered end 492 by an attachment element 493, such as a fastener. The wiper body 480 may include physical limit elements for each of the wiper arms 484. For example, the wiper arm 484 may include a limit element 494, for example, having a hook configuration, extending from the end of the arm 484. The limit element 494 is configured to engage a body limit element 495 extending from the wiper body in between the splitted legs 488 to limit the radial distance the wiper arm can move outward to protect the sensing element. The inner radial surface 497 of the wiper body 480 that defines the throughbore may include locking features for engagement with the drive sleeve 205. For example, the wiper body 480 may include one or more axial ridges 498 for receiving slotted structures 499 extending within the drive sleeve 205. The drive sleeve may be coupled with the wiper body of the second rotational wiper assembly 442 by other mechanisms, such as, adhesives, fasteners, or bonding. In one example, the configuration of the first rotational wiper assembly 440 may have the configuration of the second first rotational wiper assembly 442 and vice versa, such as the different locking features. The distal end 412A of the drive sleeve 205 may include the slotted regions 499 for insertion into the throughbore defined by the wiper body 490, where the ridges 498 are finally disposed within the slotted regions 499.

Returning to FIG. 11, the first and second rotational wiper assemblies 440, 442 are shown disposed axially to one another within the sensor mount 226 of the sensor 180. First and second rotational wiper assemblies 440, 442 are disposed relative to the sensor 180 such their respective tabs 452, 482 are aligned with the corresponding sensing bands 260A-D of the sensor 180. The device controller 170 recognizes barrel and/or drive sleeve rotational positions from the corresponding electrical signals received from the respective sensing bands 260A-D, such as described above. During the majority of barrel and/or drive sleeve rotation, the magnitude of the electrical signal to the device controller reflects where the tabs 452 and/or 482 of the wiper assemblies 440, 442 engage the corresponding sensing bands 260A-D of sensor 180. For example, when one of the tabs 452 of the wiper arms 454 of the wiper assembly 440 enter a rotary gap of the sensor 180, coming off the sensing band 260A, the other tab 452 of the other wiper arm 454 simultaneously engages the other sensing band 260B. This changed signal value, as well as the value of that signal as it further changes as the wiper moves along the angularly length of sensing band 260B, allows the controller 170 to recognize barrel rotational position until the wiper tab again engages the sensing band 260A while the other wiper tab moves off the sensing band 260B. The same can be said for the wiper assembly 442 and sensing bands 260C and 260D to allow the controller 170 to recognize the drive sleeve rotational position. In such a design, while there would always be at least one wiper arm of a wiper in contact with a sensing band for all possible rotational or angular positions of the relevant sensed member, there also will be certain rotational positions of the sensed member for which wiper engages.

Figure 14:
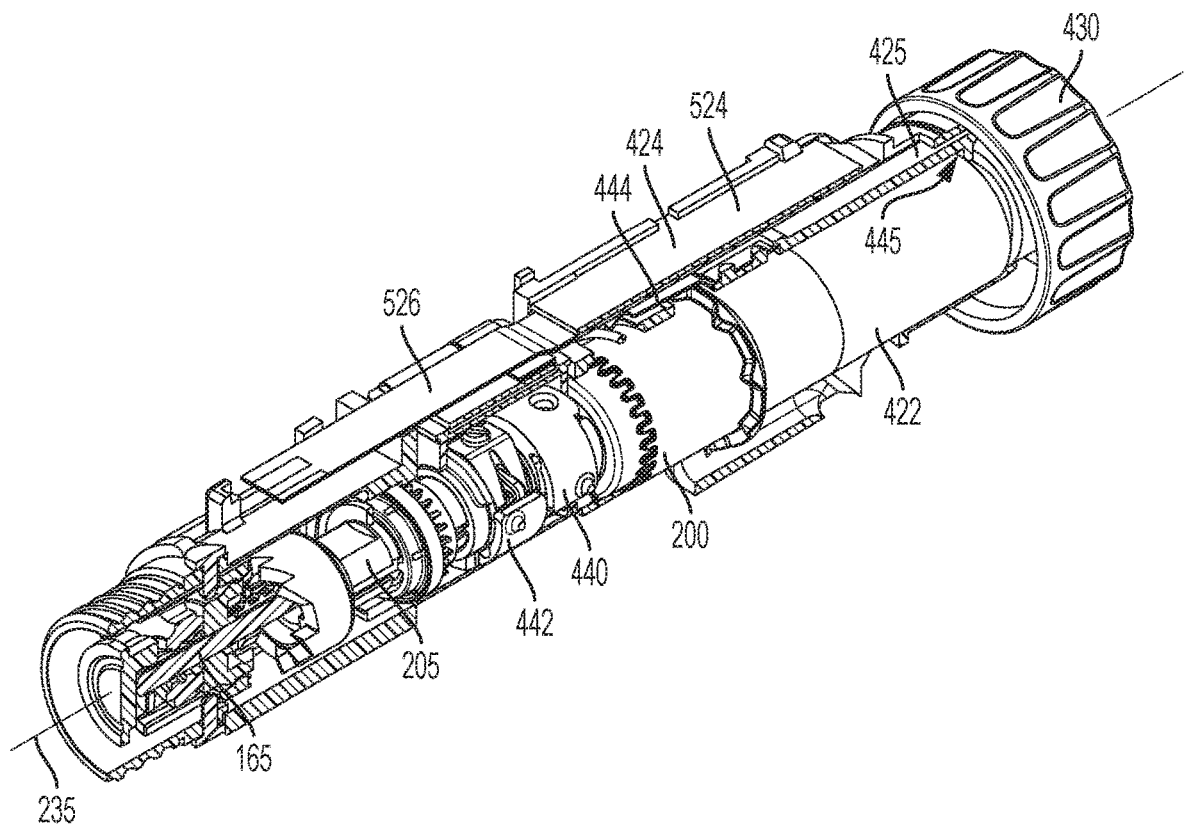
FIG. 14 is a partial perspective view, and with a region removed to reveal the interior, of the medication delivery device with sensing system of FIG. 9.
Figure 15:
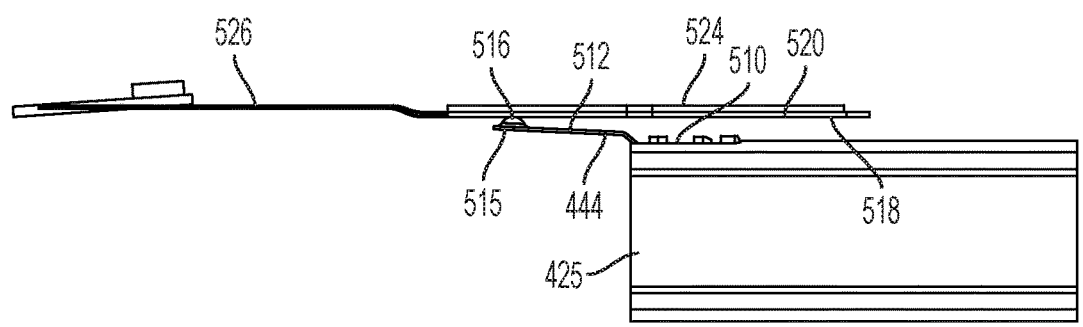
FIG. 15 is a side view of a linear wiper assembly coupled to a linear wiper sleeve of the sensing system of FIG. 9.
Figure 16:
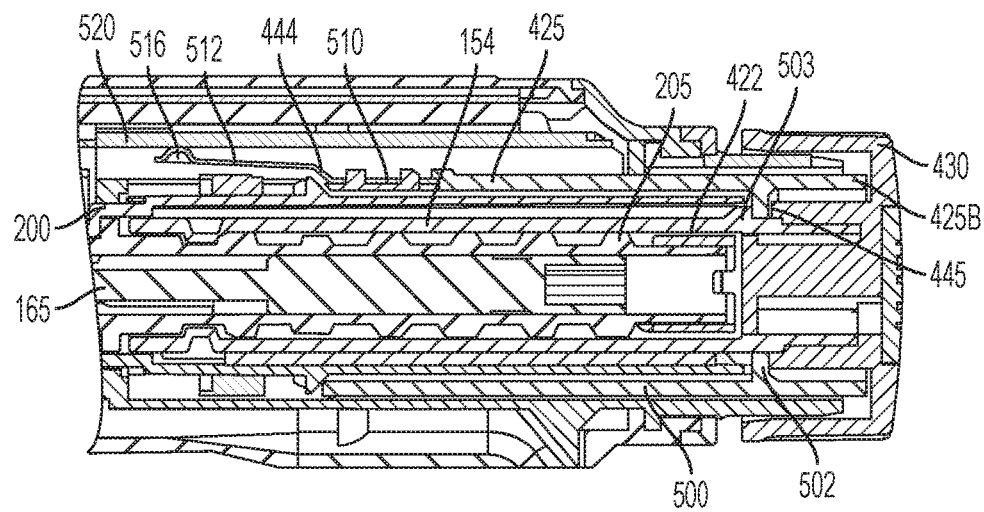
FIG. 16 is a longitudinal (Toss-sectional view taken from a callout in FIG. 2.

FIGS. 14-16 depict further aspects of the linear wiper assembly 444 and the linear wiper sleeve 425 in more detail. As described previously, the linear wiper sleeve 425 is configured to track the axial movement of the dial sleeve 412. The linear wiper sleeve 425 extends in a tubular configuration between distal and proximal ends 425A, 425B. The sidewall 500 of the sleeve 425 defines a through bore about the axis 235, which is sized and shaped to fit over, at least partially, the dial tube 154 with at least a proximal portion of the barrel 200 disposed between the linear wiper sleeve 425 and the dial tube 154. In one example, the linear wiper sleeve 425 includes an inner radial flange 502 extending from the interior surface 505 of the sidewall 500. The inner radial flange 502 is longitudinally spaced from the proximal end 425B of the sleeve 425. The distal face of the inner radial flange 502 is in engageable with a proximal face of an outer radial flange 503 extending from an exterior surface 504 of the dial tube 154 to define the thrust bearing interface 445. The exterior surface 504 of the sleeve 425 may include sliding features for engagement with the device housing or chassis housing 210 that allow for axial translation and inhibit rotation. In one example, the exterior surface 504 of the sleeve 425 includes one or more axial slide ridges 506 (four shown circumferentially spaced from one another by equal distances) that fit within slide channels (not shown) sized and shaped to receive the axial slide ridges 506, which are formed along the interior surface of the chassis housing 210. In another example, the sleeve 425 may include the slide channels and the chassis housing 210 may include the slide ridges. The proximal end 425B of the linear wiper sleeve 425 is sized and shaped such that the interior of the dose knob 430 can fit over it. The linear wiper sleeve 425 proximally translates without rotation with the dose knob 430 and dose tube 154 as result of the flanged interface 445, and without rotation due to the sliding features as the dose knob 430 is rotated, and moved proximally during dose setting as the dose knob is helically turned. The linear wiper sleeve 425 distally translates with the dose knob 430 and dose tube 154 as result of the dose knob's direct engagement with the proximal end of the linear wiper sleeve 425, and without rotation due to the sliding features as the dose knob 430 is rotated, as the dose knob 430 is pressed into the general device housing in the distal direction during dose delivery.

The linear wiper assembly 444 includes a mounting portion 510 and axially extended arm portion 512, each may be a resilient material, such as stainless steel, formed separately and coupled to one another or integrally formed as a unit structure. The linear wiper assembly 444 also includes a linear sensor element 520 against with an engaging portion of the arm portion 512 slidably contacts. The mounting portion 510 is configured to securely couple with the linear wiper sleeve 425. In one example, the coupling may be mechanical fasteners, or in the alternative, by other coupling mechanisms, such as, for example, adhesives, fasteners, or bonding. The exterior surface of the linear wiper sleeve 425 may include a recessed region sized and shaped to receive the mounting portion. In one example, the arm portion 512 is disposed farther radially outward than the mounting portion 510. Any portion of the arm portion 512 may contact the linear sensing element 520. In one example, the end 515 of the arm portion 512 may include a contacting tab 516 as the engaging portion in slidable contact with an active sensing region 518 of the linear sensing element 520 when assembled. In other examples, the engaging portion may be a tip or an undulated portion of the arm portion 512. The arm portion 512 may be biased radially outward. In one example, the arm portion includes a leaf spring configuration to generate a residual contact force to activate the linear sensing element 520. Thus in operation, with rigid mounting of the linear wiper to the linear wiper sleeve, the engaging portion of the linear wiper tracks the axial position of dial sleeve 425 with an axial locus of points.

The linear sensing element 520 is fixed securely to the chassis housing 210 or housing of the device. In one example, the chassis housing 210 includes a mounting feature 522, such as a mounting flange formed by elevated walls extending from a proximal region of the chassis housing 210. The linear sensing element 520 includes a sensing support member 524 supporting the active sensing region 518, and a sensing circuit portion 526 electrically coupled with the active sensing region 518. The sensing circuit portion 526 includes voltage input and output leads and ground leads, and such leads are in electrical communication with the processor of the controller. The sensing circuit portion 526 is arranged extending proximally from the active sensing region 518 over and beyond the sensing unit 402. The active sensing region 518 facing radially inward for engagement with the engaging portion of the arm 512. As the engaging portion of the arm 512 of the linear sensing element 520 contacts the active sensing region 518 of the linear sensing element 520 along varying positions along the effective length of the active sensing region 518, thereby communicating the axial position of the linear wiper sleeve 425 and thus dial tube 154 due to their longitudinal movement together. The sensed axial position of the dial tube 154 may correlate to an absolute position of the dial tube 154 over the effective linear length, for example, 30 mm, as a continuous encoder without sensing interruptions. In one example, the linear sensing element 520 is a variable resistive device or linear membrane potentiometer. One example of the linear sensing element 520 is Flexipot™ strip position sensor provided by Tekscan, Inc. The resistive value changes in proportion to the axial position of the dial tube 154 for both dose setting and dose delivery.

Figure 17:
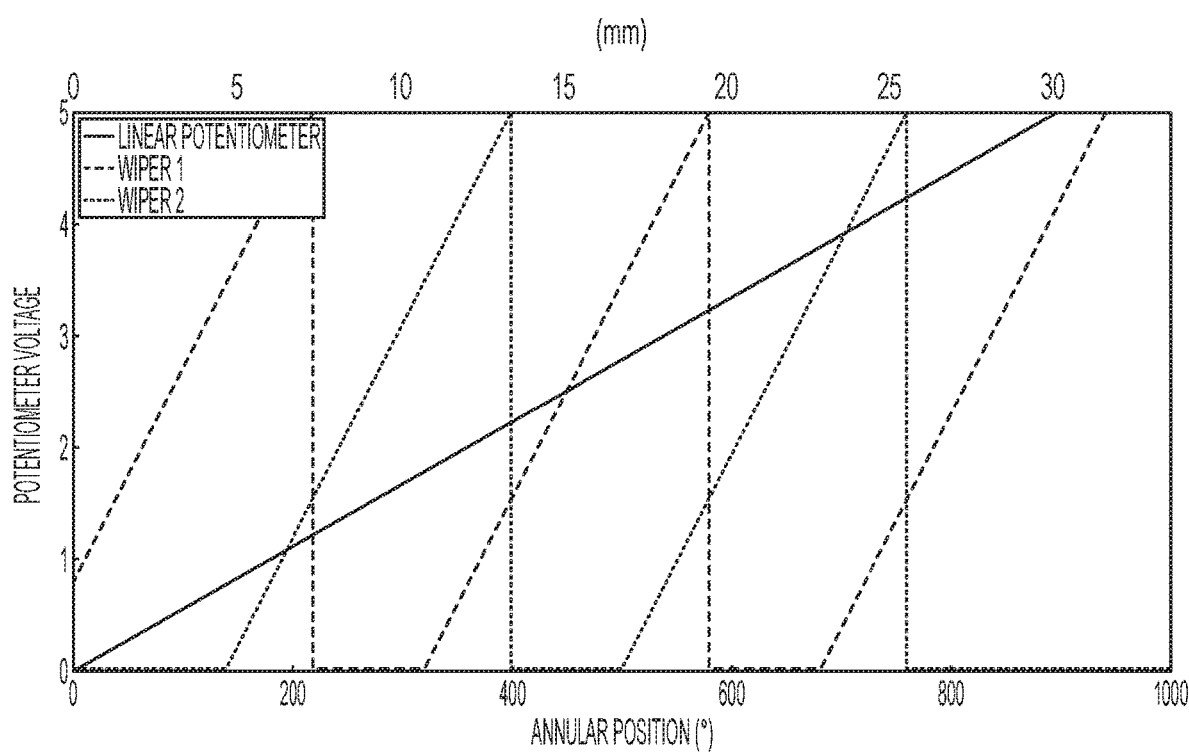
FIG. 17 is a chart illustrating the electrical signals received by the controller which are output from one of the rotational wiper assemblies of the sensed rotating parts, either the barrel or the drive sleeve, and the linear wiper assembly of the sensed sleeve part of the medication delivery device with sensing system of FIG. 9.

The sensing system 402 can combine and/or synchronize the rotational wiper assemblies 440, 442 (or wipers 185, 320) and the liner sensing element 444. FIG. 17 illustrates a simulated dual wiper output for each sensing band of the set producing independent outputs to the controller 170, thus there is adequate data for the controller software to deal with the handover period to calculate the dial tube position and to associate the dial tube position with a dose setting and/or dose delivery amount. FIG. 17 illustrates the expected output signal in volts for the angular rotational position in degrees of a wiper set (for example, tabs 452 of barrel wiper assembly 440) and a corresponding set of sensing bands (260A—"Wiper 1; 260B "Wiper 2") (the same for the dial sleeve wiper assembly 442 and sensing bands 260C, 260D) and for the linear displacement in millimeters for the linear sensor (the active sensing region 518 of the linear sensing element—"Linear Potentiometer"). FIG. 17 exaggerates for purposes of illustration the overlap or handover period. The two signals provided by the wiper assembly can be combined to provide a continuous rotary position signal over a single turn (360 degrees) range at a relatively fine resolution. The linear sensing element 444 communicates the output signal to the controller, which is indicative of the dial sleeve axial position which can be interpreted as a coarse indication of the dial sleeve rotary position over a range of multiple turns (currently 2.5 turns), based on the known pitch of the helical thread interface between the dial sleeve and drive sleeve. For example, the linear potentiometer output signal at about 2 volts correlates with component device rotating a single turn (or 360 degrees), and at about 4 volts correlates with two turns (or 720 degrees), and so forth. The combination of the rotational position of the component device and the determination of which turn based on linear position can be used to determine the dose setting and/or dose delivery. This multi-turn coarse position information can be further associated as an indication of the current number of whole turns of the dial sleeve relative to the drive sleeve. The controller can process this data with the fine single turn-rotary position signal to generate an output signal that exploits the fine resolution of the rotary sensor (s) and the multi-turn range of the linear sensor.

For example, to calculate a dose setting output the following can be processed with the controller 170. The sensing bands 260A, 260B communicate first signals, analog or digital, based on the barrel wiper first tab and second tab to the controller. The first signals are rationalized (analog to digital converter and/or signal processed) to determine if in calibration bounds and which signal is the active sensing band. The controller determines from the first signal to a dose value to clicks number for the barrel. The barrel rotates during dose setting, and the drive sleeve does not rotate during dose setting. The sensing bands 260C, 260D communicate second signals, analog or digital, based on the drive sleeve wiper first tab and second tab to the controller. The second signals are rationalized (analog to digital converter and/or signal processed) to determine if in calibration bounds and which signal is the active sensing band. The controller determines from the second signal to a dose value to clicks number for the drive sleeve. The barrel does not rotate during dose setting, and the drive sleeve rotates during dose setting. The linear sensing band communicate third signals, analog or digital, based on the dial sleeve tab to the controller. The controller determines from the third signal to a value to dial position approximation. The dial sleeve axially moves during dose setting and dose delivery. The controller determines an output display signal from the sum of full turn values to the differential does values from the first and second signals until within margin of error from linear sensor estimation. Such output display signal can be communicated to the display 140 to indicate to the user the amount of dose setting and/or delivery. The controller may also wirelessly transmit to communicate the output display signal off board to a remote device, such as mobile phone or server.

Any of the sensing systems described herein may operate to detect relative rotational positions of a single rotational device member of the drive and/or dosing assembly of the device or other rotational device component (such as, for example, the dial tube, drive sleeve, the barrel, drive screw, dial knob, carriages) to which it is coupled and generates outputs correlated to such relative rotational positions. To this end, any of the devices described herein may include a single rotational wiper assembly of any one of wiper assemblies described herein (such as subassembly with wiper 185 and beating 310, subassembly with wiper 320 and hearing 326, first rotational wiper assembly 440, or second rotational wiper assembly 442). With such configuration, the sensor mount and the sensor are modified to include a pair of sensing bands, rather than four, for contact with the respective tabs of the wiper assembly. Any of the sensing systems described herein may operate to detect relative rotational positions of more than two rotational device members of the drive and/or dosing assembly of the device or other rotational device component (such as, for example, the dial tube, drive sleeve, the barrel, drive screw, dial knob, carriages) to which it is coupled and generates outputs correlated to such relative rotational positions. To this end, any of the devices described herein may include the respective number of rotational wiper assembly of any one of wiper assemblies described herein (such as subassembly with wiper 185 and bearing 310, subassembly with wiper 320 and bearing 326, first rotational wiper assembly 440, or second rotational wiper assembly 442). With such configuration, the sensor mount and the sensor are modified to include corresponding numbers sensing bands. The device and sensing systems may further be modified to include any combination of rotational wiper assemblies described herein (such as subassembly with wiper 185 and bearing 310, subassembly with wiper 320 and bearing 326, first rotational wiper assembly 440, or second rotational wiper assembly 442). For example, the first rotational wiper assembly 440 may be combined with the subassembly with wiper 320 and bearing 326 to form at least a part of another example sensing system.

Figure 18:
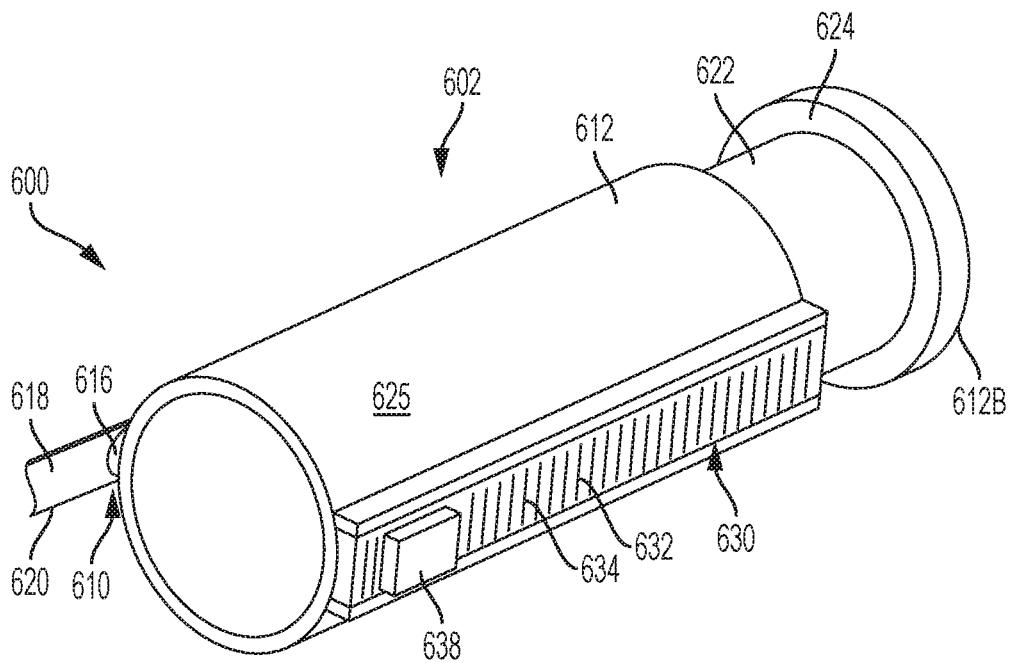
FIG. 18 is a partial perspective view of the components of another example of a sensing system for a medication delivery device.
Figure 19:
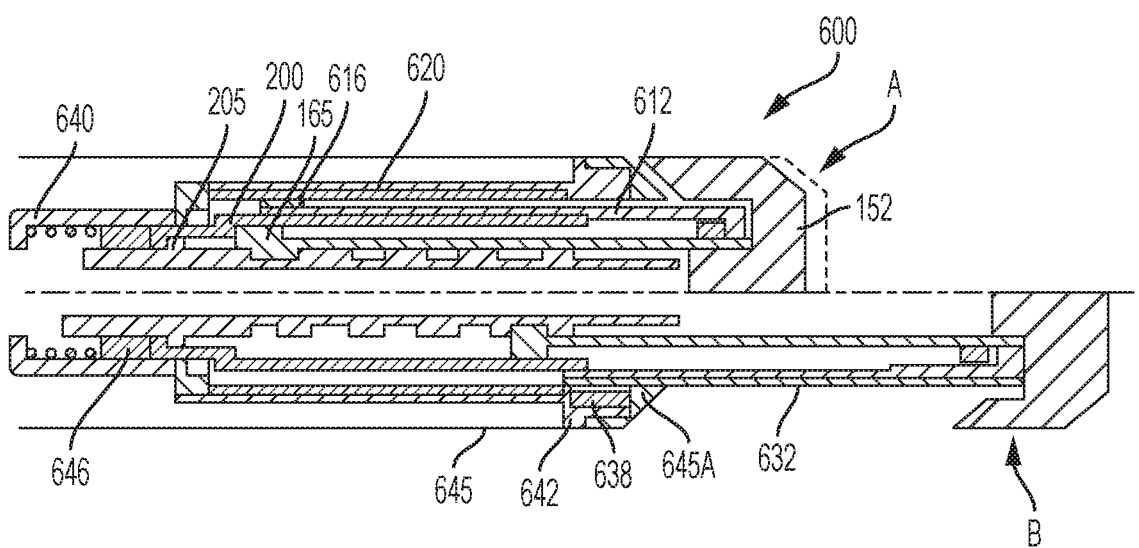
FIG. 19 is a partial longitudinal cross-sectional view of the device with the sensing system of FIG. 18 at a position zero (configuration A) and at a dosing position (configuration B)

FIGS. 18-19 shows another example of a sensing system 602 with a pair of linear sensing elements that may be included with the device of FIGS. 1-2, now referred to generally as 600 (with portions omitted for clarity). As with the device 100, the device 600 is configured to determine both the amount of the dose set and the amount of the dose delivered by operation of the device. The device 600 includes some of the same components for drug dosing and drug delivery as the device 100 described above. The sensing system 602 includes a first linear assembly 610 coupled to the linear wiper sleeve 612 configured to move axially only (allowing for rotation within small tolerances, for example, less than one degree). The linear wiper sleeve 612 is configured to track the axial movement of the dial sleeve (not shown). In one example, the first linear assembly 610 includes the same configuration as the linear wiper assembly 444, including the mounting portion (not shown) and the axially extended arm portion 616 slidably engaging an active region 618 of the linear sensor element 620 for position sensing. The linear sensor element 620 is operable to generate a first output signal that is communicated to the controller 170, and the controller is operable to determine a position value based on the first output signal. The linear wiper sleeve 612 may have the same configuration of the linear wiper sleeve 425. In another example, the linear wiper sleeve 612 may include a reduced neck region 622 proximate its proximal end 612B and a radial flange 624 along the proximal end 612B. The flange 624 engages the dial sleeve and allowing rotation of the dial sleeve relative to the linear wiper sleeve 612 that remains rotationally fixed and longitudinally movable within the chassis housing. Like the sleeve 425, the exterior surface 625 of the sleeve 612 may include sliding features (not shown) for engagement with the device housing or chassis housing that allow for axial translation and inhibit rotation. The linear wiper sleeve 612 fits over the dial tube 165, the barrel 200 and the drive sleeve 205.

The sensing system 602 includes a second linear assembly 630. The second linear assembly 630 includes a linear sensing element 632 having an active sensing region 634 disposed longitudinally along the exterior surface 625 of the sleeve 612. The active sensing region 634 includes an encoded pattern, such as, for example, ferromagnetic or electrically conducting stripes or embossments for an inductive sensor, or printed or otherwise formed ridges or detents for an optical sensor. The coded marking maybe longitudinally spaced from one another by a repetitive, fixed distance, such as, for example, 1.2 mm. The second linear assembly 630 includes a sensor element 638 disposed along the device housing or chassis housing. The sensor element 638 is operable to read the encoded pattern during relative movement of the linear sensing element fixed to the sleeve and generate a second output signal to be indicative of relative position of the dose knob. The generated signal may be analog or digital and communicated to the controller, which is operable to determine a position value based on the second signal.

FIG. 19 illustrates in the same figure configuration A of the top half of the device where the dial knob 152 is at its zero position, and configuration B of the bottom half of the device where the dial knob/dial tube is at is fully extended proximal position. In configuration A, only the first linear assembly 610 and its wiper arm/tab engaging the sensor element 620 which is disposed and affixed securely along the wall of a chassis housing 640. In configuration B, only the second linear assembly 630 is shown, with the sensor element 638 embedded within a recess 642 defined by sidewall of the chassis housing 640. The sensor element 638 may include a protective film over the recess 642 to protect the sensor 638 from debris or any other interference causing substances that would effect the sensing capability. In this example, the sensor element 638 is disposed at the proximal end 645A of the housing 645. Due to the positioning of the sensor element 638, the clicking mechanism 646 and splines associated with the device is shown repositioned near the distal end of the barrel.

The sensor element 638 may be an inductive sensor or optical sensor or other suitable sensor. An example of the sensor element 638 is a POSIC Sensor (www.posic.ch), reference ID450L. An example of a suitable optical sensor is a light source, lens and light sensor operable to translate optical impulses into electrical impulses. In addition, U.S. Pat. No. 6,043,644, the contents of which are incorporated herein by reference thereto, provides further details of the inductance sensing configuration.

Figure 20:
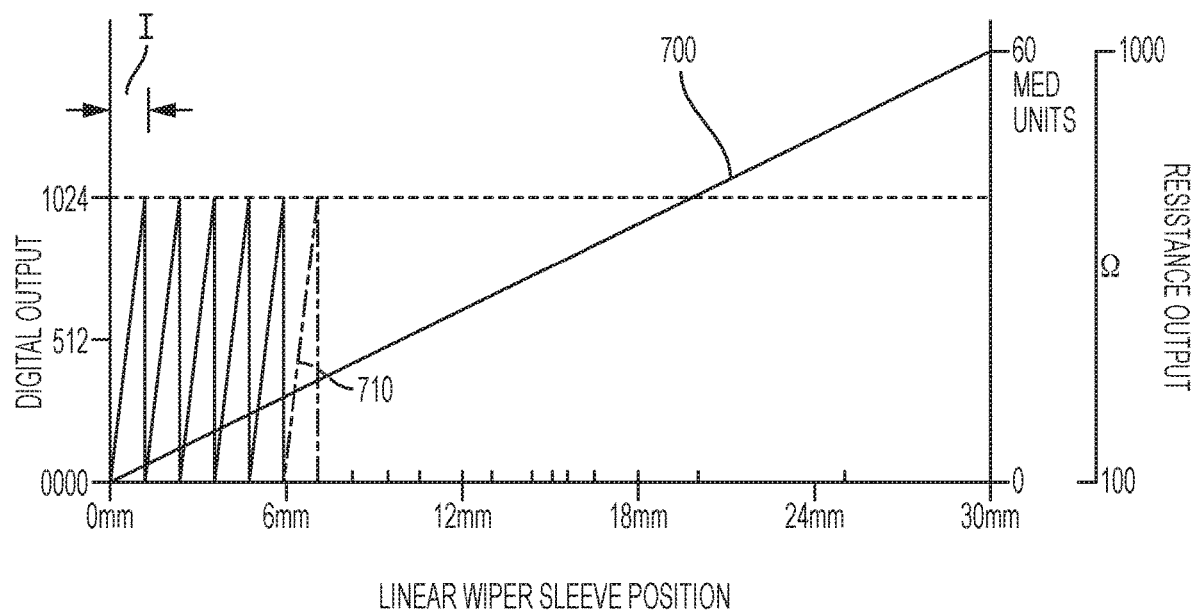
FIG. 20 is a chart illustrating the electrical signals received by the controller which are output from the linear wiper assemblies of the sensed sleeve of the medication delivery device with sensing system of FIG. 18.

One example of the sensing system 602 with both linear assemblies 610, 630 is the combination of resistive continuous linear encoder with the precision digital encoder may provide the device the ability to track both absolute position and exact position of the dial sleeve (for example, 30 mm of travel for 60 units of medicant) during dose setting and dose delivery. FIG. 20 illustrates each linear sensing assembly producing independent outputs to the controller 170, and for the controller software to calculate the dial tube position and to associate the dial tube position with a dose setting and/or dose delivery amount. FIG. 20 illustrates the expected output signal 700 for the first linear assembly 610. The expected output signal may be a continuous position signal (100 to 1000 ohms) at +/−2% FS (equals to about +/−0.6 mm). Also illustrated is the expected output signal 710 for the second linear assembly 630. The expected output signal may be an incremental position signal (digitally 0 to 1024) at increments of about 1.2 mm/1024=0.00117 mm). The two signals provided by the wiper assembly can be combined to provide a continuous rotary position signal over a single turn (360 degrees) range at a relatively fine resolution.

Any of the sensing systems described herein may operate to detect relative linear positions of a more than one longitudinally translational device member of the drive and/or dosing assembly of the device, or other device component (such as, for example, the linear sleeve, the dial tube, drive sleeve, the barrel, drive screw, dial knob, carriages) to which it is coupled and generates outputs correlated to such relative linear positions. To this end, any of the devices described herein may include a single linear wiper assembly of any of the linear wiper assemblies described herein (such as linear wiper assembly 444 or 630) atone (that is, without the rotational wiper assembly). In another example, the devices may include any one or combination of the rotational and/or linear wiper assemblies to detect relative rotational and/or linear positions of the drive and/or dosing assembly of the device or other device component.

In another example, a medication delivery device is provided for delivering medication from a cartridge having a barrel holding the medication between a movable plunger and an outlet, the medication delivery device including a main housing, a cartridge housing to hold the cartridge extending from the main housing, and a drive member including a forward distal end to engage the movable plunger. The drive member has a length extending in an axial distal direction within the main housing. The device includes a dose delivery mechanism operable to control advancement of the drive member forward within the main housing in the distal direction to move the movable plunger to deliver medication through the outlet. The dose delivery mechanism includes a first member rotatable relative to the main housing in proportion to one of an amount of a dose set and an amount of a dose delivered by operation of the medication delivery device. The first member is relatively rotatable to the main housing about an axis of rotation extending in the axial direction. The device includes a sensing system operable to detect relative rotational positions of the first member and the main housing and generate outputs correlated to such relative rotational positions. The sensing system includes a first wiper rotationally coupled to the first member and projecting in a radial direction, and a second wiper rotationally coupled to the first member and projecting in the radial direction. The sensing system includes a first sensing band and a second sensing band. The first sensing band is rotationally coupled to the main housing and circuited with an electrical power source. The first sensing band is arranged in a curved shape around the axis of rotation, having a first operational angular length. The first sensing band is disposed in the radial direction inward or outward of the first wiper for a physical contact with the first wiper as the first member rotates relative to the main housing. The first sensing band includes a first electrical strip and/or a second electrical strip being in electrical contact along the first operational angular length where the first sensing band is operationally engaged in the radial direction due to physical contact with the first wiper. The first electrical strip and/or the second electrical strip are spaced in the radial direction and out of electrical contact along the first operational angular length where the first sensing band is not operationally engaged in the radial direction due to physical contact with the first wiper, the first sensing band having an electrical characteristic correlated with where along the first operational angular length the first sensing band is operationally engaged in the radial direction due to the physical contact with the first wiper. The second sensing band is rotationally coupled to the main housing and circuited with the electrical power source. The second sensing band is arranged in a curved shape around the axis of rotation, having a second operational angular length. The second sensing band is disposed in the radial direction inward or outward of the second wiper for a physical contact with the second wiper as the first member rotates relative to the main housing. The second sensing hand includes a third electrical strip and/or a fourth electrical strip being in electrical contact along the second operational angular length where the second sensing band is operationally engaged in the radial direction due to physical contact with the second wiper. The third electrical strip and/or the fourth electrical strip being spaced in the radial direction and out of electrical contact along the second operational angular length where the second sensing band is not operationally engaged in the radial direction due to physical contact with the second wiper. The second sensing band has an electrical characteristic correlated with where along the second operational angular length the second sensing band is operationally engaged in the radial direction due to the physical contact with the second wiper. The first wiper, the second wiper, the first sensing band and the second sensing band are sized and positioned such that for at least one rotational position of the first member relative to the main housing the first wiper operationally engages the first sensing band while the second wiper does not operationally engage the second sensing band, and for at least another rotational position of the first member relative to the main housing different from the at least one rotational position the second wiper operationally engages the second sensing band while the first wiper does not operationally engage the first sensing band. The device includes a controller electrically circuited with the sensing system for separately receiving one output from the first sensing band and another output from the second sensing band to identify, based on outputs from both the first and second sensing bands of the sensing system, rotation of the first member relative to the main housing indicative of at least one of the amount of the dose set and the amount of the dose delivered by operation of the medication delivery device. The first sensing band may be disposed radially outward of the first wiper and the second sensing band may be disposed radially outward of the second wiper. The first and second sensing bands may be disposed on a base component that is rotatably fixed and axially movable relative to the main housing. Each of the first and second operational angular lengths may extend only partially around a circumference of the first member. Each of the first operational angular length and the second operational angular length may extend less than 220 degrees around the circumference of the first member. Each of the first operational angular length and the second operational angular length may extend at least 180 degrees around the circumference of the first member. The first operational angular length and the second operational angular length may span the same angular distance and may be positioned around a same circumferential portion of different axial segments of the first member. The first wiper and the second wiper may be angularly spaced about the axis of rotation. The first wiper and the second wiper may be angularly spaced 180 degrees about the axis of rotation. The first wiper and the second wiper may be fixedly coupled to the first member to move axially therewith. The first member may be axially movable within the main housing during operation of the medication delivery device, and wherein the base component and thereby the first sensing band and the second sensing band are constrained to move axially with the first member to maintain alignment of the first wiper with the first sensing band and the second wiper with the second sensing band.

While embodiments of the invention has been illustrated and described in detail in the drawings and foregoing description, the same is to be considered as illustrative and not restrictive in character. For example, device sensing module can sense dose setting amounts if adapted to work with a device portion having suitable parts that experience relative rotation during dose setting. This application is therefore intended to cover any variations, uses or adaptations of the invention using its general principles. Further, this application is intended to cover such departures from the present disclosure as come within known or customary practice in the art to which this present disclosure pertains. All changes, equivalents, and modifications that come within the spirit of the inventions defined by the claims included herein are desired to be protected.

Various aspects are described in this disclosure, which include, but are not limited to, the following aspects:

1. A medication delivery device comprising: a first member and a second member rotatable relative to the first member about an axis of rotation in proportion to at least one of an amount of a dose set and an amount of a dose delivered by operation of the medication delivery device; a wiper assembly coupled to the first member, the wiper assembly having a pair of radially projecting wipers; a first electrically operable sensing band and a second electrically operable sensing band each coupled to the second member, each of the sensing bands arranged in a curved shape and radially disposed relative to and in contacting relationship with the wipers, respectively, wherein, during relative rotation between the first and second members, each of the sensing bands is operable to generate outputs associated with the relative angular position of the wiper along an operational angular length of each of the sensing bands that is indicative of relative rotational positions of the first and second members; and a controller electrically coupled with the sensing band to determine, based on the outputs generated by each of the sensing bands, at least one of the amount of the dose set and the amount of the dose delivered by operation of the medication delivery device.
2. The medication delivery device of aspect 1, wherein one of the wipers extend axially farther than the other of the wipers.
3. The medication delivery device of any one of aspects 1-2, wherein the sensing bands are discrete bands disposed axially relative to one another.
4. The medication delivery device of any one of aspects 1-3, wherein the wiper assembly includes a cylindrical wiper body defining a throughbore sized to receive, at least a portion of the first member.
5. The medication delivery device of aspect 4, wherein the wiper assembly includes biasable arms coupled to a circumferential surface of the cylindrical wiper body, wherein one of the arms includes a tab to define one of the wipers, and another of the arms includes a tab to define another of the wipers.
6. The medication delivery device of aspect 5, wherein the arms of the wipers are disposed along opposite sides of the circumferential surface of the cylindrical wiper body.
7. The medication delivery device of aspect 6, wherein the tabs of the wipers are positioned axially offset from one another and located along opposite sides of a central plane of the cylindrical wiper body.
8. The medication delivery device of any one of aspects 4-7, wherein the wiper assembly includes a biasing member disposed to bias at least one of the arms of the wipers radially outward.
9. The medication delivery device of any one of aspects 4-8, wherein the wiper assembly includes a limit element engageable with a body element of the cylindrical wiper body to limit the radial outer extent of the arms.
10. The medication delivery device of any one of aspects 1-9, wherein the cylindrical wiper body includes locking features for secure coupling to the first member.
11. The medication delivery device of aspect 5, wherein the arms project longitudinally from the cylindrical wiper body.
12. The medication delivery device of aspect 11, wherein the wiper assembly includes a bearing securely coupled between the cylindrical wiper body and the first member.
13. The medication delivery device of any one of aspects 1-12 further comprising: a linear sleeve coupled to the first member; a linear wiper assembly coupled to the linear sleeve, the linear wiper assembly having a radially projecting linear wiper; and an electrically operable sensing linear band disposed within a device housing, the sensing linear band radially disposed relative to and in contacting relationship with the linear wiper, wherein, during relative longitudinal displacement between the linear sleeve and the device housing, the sensing linear band operable to generate outputs associated with a relative longitudinal position of the linear wiper along an operational angular length of the sensing linear band that is indicative of the relative longitudinal position, wherein the controller is electrically coupled with the sensing linear band to determine, based on the outputs generated by the sensing linear band, at least one of the amount of the dose set and the amount of the dose delivered by operation of the medication delivery device.
14. The medication delivery device of aspect 13, wherein the linear sleeve is disposed radially outward relative to the first member, wherein the linear sleeve is configured for longitudinal movement.
15. The medication delivery device of any one of aspects 1-14, further comprising a sensor mount having a U-configuration and a radially inwardly facing surface to support the sensing bands that are arranged in the curved shape.
16. The medication delivery device of any one of aspects 1-15 further comprising: a linear sleeve coupled to the first member; a linear wiper assembly coupled to the linear sleeve; a sensing linear encoded band disposed along the linear sleeve; and an electrically operable proximity sensor disposed within a device housing radially outside of the sensing linear encoded band, wherein, during relative longitudinal displacement between the linear sleeve and the device housing, the proximity sensor is operable to generate outputs associated with a relative longitudinal position of the linear sleeve that is indicative of the relative longitudinal position, wherein the controller is electrically coupled with the proximity sensor to determine, based on the outputs generated by the sensing linear band, at least one of the amount of the dose set and the amount of the dose delivered by operation of the medication delivery device.
17. A medication delivery device comprising: a device housing including a first member and a second member rotatable relative to the first member about an axis of rotation in proportion to an amount of a dose set by operation of the medication delivery device, and a third member rotatable relative, to the second member about the axis of rotation in proportion to an amount of a dose delivered by operation of the medication delivery device; a first rotational wiper component coupled to the first member, the first rotational wiper component including a pair of first wipers projecting in a radial direction; a second rotational wiper component coupled to the third member, the second rotational wiper component including a pair of second wipers projecting in a radial direction; a pair of electrically operable first sensing bands coupled to the second member, and a pair of electrically operable second sensing bands coupled to the second member, wherein each of the pairs of the first and second sensing bands arranged in a curved shape and disposed axially relative to one another in a contacting relationship with corresponding first and second wipers, wherein, during relative rotation between the first and second members and relative rotation between the third and second members, the pairs of the first and second sensing bands are operable to generate outputs associated with the relative angular position of the corresponding first and second rotational wipers along an operational angular length of the respective first and second sensing bands that is indicative of relative rotational positions of the first and second members and the third and second members; and a controller electrically coupled with the pairs of the first and second sensing bands to determine, based on the outputs generated by the first and second sensing bands, the amount of the dose set and the amount of the dose delivered by operation of the medication delivery device.

18. The medication delivery device of aspect 17, wherein each of the first and second rotational wiper components includes a cylindrical wiper body defining a throughbore sized to receive at least a portion of the first member and the third member, respectively.

19. The medication delivery device of aspect 18, wherein each of the first wipers include an axially extended arm coupled to a circumferential surface of the cylindrical wiper body of the first rotational wiper component, and wherein each of the second wipers include an axially extended arm coupled to a circumferential surface of the cylindrical wiper body of the second rotational wiper component.

20. The medication delivery device of any one of aspects 17-19, further comprising a sensor mount assembly defining the second member, wherein the first and third members include a tubular configuration, and the third member is disposed through the first member and is extended distally beyond a distal end of the first member, wherein the first rotational wiper is coupled to the distal end of the first member and sized to fit over the third member, wherein the second rotational wiper is coupled along and over the third member, wherein the sensor mount assembly sized and shaped to house the first and second rotational wipers that are axially adjacent to one another and the pairs of the first and second sensing bands.

21. The medication delivery device of any one of aspects 17-20 further comprising a linear sleeve coupled to the first member, a linear wiper assembly coupled to the linear sleeve, the linear wiper assembly having a radially projecting linear wiper, and an electrically operable sensing linear band disposed within the device housing, the sensing linear band radially disposed relative to and in contacting relationship with the linear wiper, wherein, during relative longitudinal displacement between the linear sleeve and the device housing, the sensing linear band operable to generate outputs associated with the relative linear position of the linear wiper along an operational angular length of the sensing linear band that is indicative of the relative longitudinal position, wherein the controller is electrically coupled with the sensing linear band to determine, based on the outputs generated by the sensing linear band, at least one of the amount of the dose set and the amount of the dose delivered by operation of the medication delivery device.

22. The medication delivery device of any one of aspects 17-21, further comprising a dose knob and an dose tube operatively coupled to one another, wherein the linear sleeve is disposed radially outward relative to the first member and the dose tube, wherein the linear sleeve is configured for longitudinal movement in a proximal direction during rotation of the dose knob and the dose tube during dose setting, wherein the linear sleeve is configured for longitudinal movement in a distal direction during distal translation of the dose knob and the dose tube during dose delivery.

23. A medication delivery device for delivering medication from a cartridge having a barrel holding the medication between a movable plunger and an outlet, the medication deliver device comprising: a main housing; a cartridge housing for holding the cartridge extending from the main housing; a drive member including a forward end for engaging the movable plunger, the drive member having a length extending in an axial direction within the main housing; a dose delivery mechanism for controlling advancement of the drive member forward within the main housing in the axial direction to move the movable plunger for delivering medication through the outlet, the dose delivery mechanism including a first rotatable member rotatable relative to the main housing about a rotational axis in proportion to one of an amount of a dose set and an amount of a dose delivered by operation of the medication delivery device; a sensing system operable to detect relative rotational positions of the first rotational member and the main housing and generate outputs correlated to such relative rotational positions, the sensing system comprising: a first wiper assembly coupled to the first rotational member, the wiper assembly having a pair of contacting portions projecting in an outer radial direction; a pair of electrically operable first sensing bands coupled to the main housing, curvedly arranged about the rotational axis in an outer radial direction relative to the first wiper assembly for physical contact therewith during rotation of the first rotatable member relative to the main housing; and a controller in electrical communication with the sensing system to determine, based on outputs of the sensing system, at least one of the amount of the dose set and the amount of the dose delivered by operation of the medication delivery device.

24. The medication delivery device of aspect 23, wherein the first rotatable member is rotatable relative to the main housing about the rotational axis in proportion to the amount of the dose set, wherein the dose delivery mechanism further includes a second rotatable member rotatable relative to the main housing about the rotational axis in proportion to the amount of the dose delivered, wherein the sensing system further comprises a second wiper assembly coupled to the second rotational member, the second wiper assembly includes a pair of contacting portions projecting in an outer radial direction, and a pair of electrically operable second sensing bands coupled to the main housing, curvedly arranged about the rotational axis in an outer radial direction relative to the second wiper assembly for physical contact therewith during rotation of the second rotatable member relative to the main housing, wherein the controller is configured to determine, based on outputs of the sensing system, the amount of the dose set and the amount of the dose delivered by operation of the medication delivery device.

25. The medication delivery device of any one of aspects 23-24, wherein the sensing system includes a linear sleeve coupled about the first rotatable member, a linear wiper assembly having a radially projecting linear wiper coupled to the linear sleeve, and an electrically operable sensing linear band disposed within the main housing, the sensing linear band radially disposed relative to and in contacting relationship with the linear wiper, wherein, during relative longitudinal displacement between the linear sleeve and the main housing, the sensing linear band operable to generate outputs associated with the relative linear position of the linear wiper along an operational angular length of the sensing linear band that is indicative of the relative longitudinal position, wherein the controller is electrically coupled with the sensing linear band to determine, based on the outputs generated by the sensing linear band, at least one of the amount of the dose set and the amount of the dose delivered by operation of the medication delivery device.

26. A medication delivery device for delivering medication from a cartridge having a barrel holding the medication between a movable plunger and an outlet, the medication delivery device comprising: a main housing; a cartridge housing to hold the cartridge extending from the main housing; a drive member including a distal end to engage the movable plunger, the drive member having a length extending in an axial direction within the main housing; a close delivery mechanism operable to control advancement of the drive member within the main housing in a distal axial direction for moving the movable plunger to deliver medication through the outlet, the dose delivery mechanism including a first member rotatable relative to the main housing in proportion to one of an amount of a dose set and an amount of a dose delivered by operation of the medication delivery device, the first member relatively rotatable to the main housing about a rotational axis extending in the axial direction; a sensing system operable to detect relative rotational positions of the first member and the main housing and generate outputs correlated to such relative rotational positions, the sensing system comprising a first wiper rotationally coupled to the first member and projecting in a radial direction, a second wiper rotationally coupled to the first member and projecting in the radial direction, a first sensing band rotationally coupled to the main housing and circuited with an electrical power source, the first sensing band arranged around the rotational axis and having a first operational angular length, the first sensing band disposed in the radial direction outward of the first wiper for a physical contact with the first wiper as the first member rotates relative to the main housing, the first sensing band being in electrical contact along the first operational angular length where the first sensing band is operationally engaged in the radial direction due to physical contact with the first wiper, and out of electrical contact along the first operational angular length where the first sensing band is not operationally engaged in the radial direction due a lack of physical contact with the first wiper, the first sensing band having an electrical characteristic correlated with where along the first operational angular length the first sensing band is operationally engaged in the radial direction due to the physical contact with the first wiper, and a second sensing band rotationally coupled to the main housing and circuited with the electrical power source, the second sensing band arranged around the rotational axis and having a second operational angular length, the second sensing band disposed in the radial direction outward of the second wiper for a physical contact with the second wiper as the first member rotates relative to the main housing, the second sensing band being in electrical contact along the second operational angular length where the second sensing band is operationally engaged in the radial direction due to physical contact with the second wiper, and out of electrical contact along the second operational angular length where the second sensing band is not operationally engaged in the radial direction due to a lack of physical contact with the second wiper, the second sensing band having an electrical characteristic correlated with where along the second operational angular length the second sensing band is operationally engaged in the radial direction due to the physical contact with the second wiper, wherein the first wiper, the second wiper, the first sensing band and the second sensing band are sized and positioned such that for at least one rotational position of the first member relative to the main housing the first wiper operationally engages the first sensing band while the second wiper does not operationally engage the second sensing band, and for at least another rotational position of the first member relative to the main housing different from the at least one rotational position the second wiper operationally engages the second sensing band while the first wiper does not operationally engage the first sensing band; and a controller electrically circuited with the sensing system for separately receiving one output from the first sensing band and another output from the second sensing band to identify, based on outputs from both the first and second sensing bands of the sensing system, rotation of the first member relative to the main housing indicative of at least one of the amount of the dose set and the amount of the dose delivered by operation of the medication delivery device.

27. The medication delivery device of aspect 26 wherein the first and second sensing bands are disposed on a sensor mount component that is rotatably fixed and axially movable relative to the main housing.

28. The medication delivery device of any one of aspects 26-27 wherein each of the first and second operational angular lengths extends only partially around a circumference of the first member.

29. The medication delivery device of any one of aspects 26-28 wherein each of the first operational angular length and the second operational angular length extends less than 220 degrees around the circumference of the first member.

30. The medication delivery device of any one of aspects 26-28 wherein each of the first operational angular length and the second operational angular length extends at least 180 degrees around the circumference of the first member.

31. The medication delivery device of any one of aspects 26-30 wherein the first operational angular length and the second operational angular length span the same angular distance and are positioned axially adjacent to one another.

32. The medication delivery device of any one of aspects 26-31 wherein the first wiper and the second wiper are angularly spaced about the rotational axis.

33. The medication delivery device of any one of aspects 26-32 wherein the first wiper and the second wiper are angularly spaced 180 degrees about the rotational axis.

34. The medication delivery device of any one of aspects 1-33 wherein the first wiper and the second wiper are fixedly coupled to the first member to move axially therewith, the first member axially movable within the main housing during operation of the medication delivery device, and wherein the sensor mount component with the first sensing band and the second sensing band are constrained to move axially with the first member to maintain alignment of the first wiper with the first sensing band and the second wiper with the second sensing band.

35. The medication delivery device of any one of aspects 26-34 wherein the sensor mount component comprises a U-shaped configuration, including a radially inwardly facing surface to support the first and second sensing bands in a curved shape.

We claim:

1. A medication delivery device comprising:
    a first member and a second member rotatable relative to the first member about an axis of rotation in proportion to at least one of an amount of a dose set and an amount of a dose delivered by operation of the medication delivery device;
    a wiper assembly coupled to said first member, the wiper assembly having a pair of radially projecting wipers, wherein the wiper assembly includes:
        a cylindrical wiper body defining a throughbore sized to receive at least a portion of the first member,
        biasable arms coupled to a circumferential surface of the cylindrical wiper body, wherein one of said arms includes a tab to define one of said wipers, and another of said arms includes a tab to define another of said wipers, and
        a biasing member disposed to bias at least one of said arms radially outwards;
    a first electrically operable sensing band and a second electrically operable sensing band each coupled to said second member, each of said sensing bands arranged in a curved shape and radially disposed relative to and in contacting relationship with a corresponding one of said wipers, wherein, each of said sensing bands is continuously conductive such that, throughout relative rotation between said first and second members, at least one of said sensing bands is in contact with said sensing band's corresponding wiper, thereby generating a continuously varying output associated with a relative angular position of said corresponding one of said wipers along an operational angular length of said sensing band that is indicative of a relative rotational position of said first and second members; and
    a controller electrically coupled with said sensing bands to determine, based on the output generated by each of said sensing bands, at least one of the amount of the dose set and the amount of the dose delivered by operation of the medication delivery device.

2. The medication delivery device of claim 1, wherein one of said wipers extends axially farther than the other of said wipers.

3. The medication delivery device of claim 1, wherein said sensing bands are discrete bands disposed axially relative to one another.

4. The medication delivery device of claim 1, wherein said arms of said wiper assembly are disposed along opposite sides of the circumferential surface of the cylindrical wiper body.

5. The medication delivery device of claim 4, wherein said tabs of said arms are positioned axially offset from one another and located along opposite sides of a central plane of the cylindrical wiper body.

6. The medication delivery device of claim 1, wherein the wiper assembly includes a limit element engageable with a body element of the cylindrical wiper body to limit a radial outer extent of said arms.

7. The medication delivery device of claim 1, wherein the cylindrical wiper body includes locking features for secure coupling to the first member.

8. The medication delivery device of claim 1, wherein said arms project longitudinally from the cylindrical wiper body.

9. The medication delivery device of claim 8, wherein the wiper assembly includes a bearing securely coupled between the cylindrical wiper body and the first member.

10. The medication delivery device of claim 1 further comprising:
    a linear sleeve coupled to the first member;
    a linear wiper assembly coupled to the linear sleeve, the linear wiper assembly having a radially projecting linear wiper; and
    an electrically operable sensing linear band disposed within a device housing, said sensing linear band radially disposed relative to and in contacting relationship with said linear wiper, wherein, during relative longitudinal displacement between the linear sleeve and the device housing, said sensing linear band is operable to generate an output associated with a relative longitudinal position of said linear wiper along an operational sensing length of said sensing linear band that is indicative of said relative longitudinal position, wherein the controller is electrically coupled with said sensing linear band to determine, based on the output generated by said sensing linear band, at least one of the amount of the dose set and the amount of the dose delivered by operation of the medication delivery device.

11. The medication delivery device of claim 10, wherein the linear sleeve is disposed radially outward relative to the first member, wherein the linear sleeve is configured for longitudinal movement.

12. The medication delivery device of claim 1, further comprising a sensor mount having a U-configuration curved shape and a radially inwardly facing surface to support said sensing bands that are arranged in the curved shape.

13. The medication delivery device of claim 1 further comprising:
    a linear sleeve coupled to the first member;
    a sensing linear encoded band disposed along the linear sleeve; and
    an electrically operable sensor disposed within a device housing radially outside of the sensing linear encoded band, wherein, during relative longitudinal displacement between the linear sleeve and the device housing, said electrically operable sensor is operable to generate an output associated with a longitudinal position of said sensing linear encoded band relative to said electrically operable sensor, wherein the controller is electrically coupled with said electrically operable sensor to determine, based on the output generated by said electrically operable sensor, at least one of the amount of the dose set and the amount of the dose delivered by operation of the medication delivery device.

14. The medication delivery device of claim 1, wherein said second member is a main housing of the medication delivery device, the device further comprising:
    a cartridge having a barrel holding a medication between a movable plunger and an outlet;
    a cartridge housing for holding the cartridge extending from said main housing;

a drive member including a forward end for engaging the movable plunger, said drive member having a length extending in an axial direction within the main housing; and a dose delivery mechanism for controlling advancement of said drive member forward within the main housing in the axial direction to move the movable plunger for delivering medication through said outlet, said dose delivery mechanism including said first member.

15. The medication delivery device of claim 1, wherein each of said sensing bands are sized and positioned such that for at least one rotational position of said first member relative to said second member a first wiper of said pair of wipers operationally engages said first sensing band while a second wiper of said pair of wipers does not operationally engage said second sensing band, and for at least another rotational position of said first member relative to said second member different from the at least one rotational position said second wiper operationally engages said second sensing band while said first wiper does not operationally engage said first sensing band.

16. The medication delivery device of claim 15, wherein said second member is a main housing of said medication delivery device, and wherein said first and second sensing bands are disposed on a sensor mount component that is rotatably fixed and axially movable relative to said main housing.

17. The medication delivery device of claim 16, wherein the operational angular length of each of said sensing band extends only partially around a circumference of said first member.

18. The medication delivery device of claim 17, wherein the operational angular length of each of said sensing band extends less than 220 degrees around said circumference of said first member.

19. The medication delivery device of claim 17, wherein the operational angular length of each of said sensing band extends at least 180 degrees around said circumference of said first member.

20. The medication delivery device of claim 16, wherein said pair of wipers are fixedly coupled to said first member to move axially therewith, said first member axially movable within said main housing during operation of the medication delivery device, and wherein said sensor mount component with said first and second sensing bands are constrained to move axially with said first member to maintain alignment between said first and second sensing bands and said pair of wipers.

* * * * *